United States Patent
Pool et al.

(10) Patent No.: US 8,382,756 B2
(45) Date of Patent: Feb. 26, 2013

(54) EXTERNAL ADJUSTMENT DEVICE FOR DISTRACTION DEVICE

(75) Inventors: Scott Pool, Laguna Hills, CA (US); Blair Walker, Mission Viejo, CA (US); Arvin Chang, West Covina, CA (US)

(73) Assignee: Ellipse Technologies, Inc., Irvine, CA (US)

( * ) Notice: Subject to any disclaimer, the term of this patent is extended or adjusted under 35 U.S.C. 154(b) by 376 days.

(21) Appl. No.: 12/615,855

(22) Filed: Nov. 10, 2009

(65) Prior Publication Data

US 2010/0121323 A1  May 13, 2010

Related U.S. Application Data

(60) Provisional application No. 61/113,086, filed on Nov. 10, 2008, provisional application No. 61/240,071, filed on Sep. 4, 2009.

(51) Int. Cl.
*A61B 17/56* (2006.01)

(52) U.S. Cl. ............... 606/54; 606/57; 600/407

(58) Field of Classification Search ............... 600/407; 606/53, 54, 57
See application file for complete search history.

(56) References Cited

U.S. PATENT DOCUMENTS

| | | |
|---|---|---|
| 2,702,031 A | 2/1955 | Wenger |
| 3,810,259 A | 5/1974 | Summers |
| 3,976,060 A | 8/1976 | Hildebrandt et al. |
| 4,078,559 A | 3/1978 | Nissinen |
| 4,448,191 A | 5/1984 | Rodnyansky et al. |
| 4,658,809 A | 4/1987 | Ulrich |
| 4,854,304 A | 8/1989 | Zielke |
| 5,010,879 A | 4/1991 | Moriya et al. |
| 5,030,235 A | 7/1991 | Campbell, Jr. |
| 5,092,889 A | 3/1992 | Campbell, Jr. |
| 5,261,908 A | 11/1993 | Campbell, Jr. |
| 5,263,955 A | 11/1993 | Baumgart et al. |
| 5,290,289 A | 3/1994 | Sanders et al. |
| 5,336,223 A | 8/1994 | Rogers |
| 5,466,261 A | 11/1995 | Richelsoph |
| 5,573,012 A * | 11/1996 | McEwan ............... 600/595 |
| 5,575,790 A | 11/1996 | Chen et al. |
| 5,626,579 A | 5/1997 | Muschler et al. |
| 5,632,744 A | 5/1997 | Campbell, Jr. |
| 5,659,217 A | 8/1997 | Petersen |
| 5,672,175 A | 9/1997 | Martin |
| 5,704,939 A | 1/1998 | Justin |

(Continued)

FOREIGN PATENT DOCUMENTS

| | | |
|---|---|---|
| DE | 8515687 | 12/1985 |
| DE | 102005045070 A1 | 4/2007 |

(Continued)

OTHER PUBLICATIONS

PCT International Search Report for PCT/US2009/060266, Applicant: Ellipse Technologies, Inc., Form PCT/ISA/220, dated Dec. 10, 2009 (4 pages).

(Continued)

*Primary Examiner* — Ellen C Hammond
(74) *Attorney, Agent, or Firm* — Vista IP Law Group LLP

(57) ABSTRACT

A method of positioning an external adjustment device relative to a patient includes placing a magnetic viewing sheet adjacent to a patient and identifying the location of an implanted magnetic assembly using the magnetic viewing sheet by visualizing a magnetic image of the implanted magnetic assembly in the magnetic viewing sheet. The external adjustment device is placed on the patient adjacent to the location where the magnetic image was located.

5 Claims, 14 Drawing Sheets

U.S. PATENT DOCUMENTS

| | | | |
|---|---|---|---|
| 5,720,746 A | 2/1998 | Soubeiran | |
| 5,762,599 A | 6/1998 | Sohn | |
| 5,800,434 A | 9/1998 | Campbell, Jr. | |
| 5,961,553 A | 10/1999 | Coty et al. | |
| 6,033,412 A | 3/2000 | Losken et al. | |
| 6,106,525 A | 8/2000 | Sachse | |
| 6,200,317 B1 | 3/2001 | Aalsma et al. | |
| 6,234,956 B1 | 5/2001 | He et al. | |
| 6,331,744 B1 | 12/2001 | Chen et al. | |
| 6,336,929 B1 | 1/2002 | Justin | |
| 6,358,283 B1 | 3/2002 | Hogfors et al. | |
| 6,417,750 B1 | 7/2002 | Sohn | |
| 6,554,831 B1 | 4/2003 | Rivard et al. | |
| 6,765,330 B2 | 7/2004 | Baur | |
| 6,796,984 B2 | 9/2004 | Soubeiran | |
| 6,835,207 B2 | 12/2004 | Zacouto et al. | |
| 6,849,076 B2 | 2/2005 | Blunn et al. | |
| 6,918,910 B2 | 7/2005 | Smith et al. | |
| 7,029,472 B1 | 4/2006 | Fortin | |
| 7,135,022 B2 | 11/2006 | Kosashvili et al. | |
| 7,763,053 B2 * | 7/2010 | Gordon | 606/258 |
| 7,862,502 B2 * | 1/2011 | Pool et al. | 600/37 |
| 8,043,290 B2 * | 10/2011 | Harrison et al. | 606/60 |
| 8,137,349 B2 * | 3/2012 | Soubeiran | 606/63 |
| 2002/0050112 A1 | 5/2002 | Koch et al. | |
| 2003/0144669 A1 | 7/2003 | Robinson | |
| 2004/0193266 A1 | 9/2004 | Meyer et al. | |
| 2005/0055025 A1 | 3/2005 | Zacouto et al. | |
| 2005/0113831 A1 | 5/2005 | Franck et al. | |
| 2005/0143766 A1 | 6/2005 | Bachmann et al. | |
| 2005/0234448 A1 | 10/2005 | McCarthy | |
| 2005/0246034 A1 | 11/2005 | Soubeiran | |
| 2005/0251109 A1 | 11/2005 | Soubeiran | |
| 2005/0261779 A1 | 11/2005 | Meyer | |
| 2005/0272976 A1 | 12/2005 | Tanaka et al. | |
| 2006/0004459 A1 | 1/2006 | Hazebrouck et al. | |
| 2006/0009767 A1 | 1/2006 | Kiester | |
| 2006/0036323 A1 | 2/2006 | Carl et al. | |
| 2006/0036324 A1 | 2/2006 | Sachs et al. | |
| 2006/0047282 A1 | 3/2006 | Gordon | |
| 2006/0052782 A1 | 3/2006 | Morgan et al. | |
| 2006/0058792 A1 | 3/2006 | Hynes | |
| 2006/0069447 A1 | 3/2006 | DiSilvestro | |
| 2006/0074448 A1 * | 4/2006 | Harrison et al. | 606/237 |
| 2006/0079897 A1 | 4/2006 | Harrison et al. | |
| 2006/0136062 A1 | 6/2006 | DiNello et al. | |
| 2006/0155279 A1 | 7/2006 | Ogilvie | |
| 2006/0195087 A1 | 8/2006 | Sacher et al. | |
| 2006/0195088 A1 | 8/2006 | Sacher et al. | |
| 2006/0271107 A1 | 11/2006 | Harrison et al. | |
| 2007/0010887 A1 | 1/2007 | Williams et al. | |
| 2007/0021644 A1 * | 1/2007 | Woolson et al. | 600/9 |
| 2007/0031131 A1 | 2/2007 | Griffitts | |
| 2007/0050030 A1 | 3/2007 | Kim | |
| 2007/0173837 A1 | 7/2007 | Chan et al. | |
| 2007/0179493 A1 | 8/2007 | Kim | |
| 2007/0191846 A1 | 8/2007 | Bruneau et al. | |
| 2007/0213751 A1 | 9/2007 | Scirica et al. | |
| 2007/0233098 A1 | 10/2007 | Mastrorio et al. | |
| 2007/0239161 A1 | 10/2007 | Giger et al. | |
| 2007/0255088 A1 | 11/2007 | Jacobson et al. | |
| 2007/0270803 A1 | 11/2007 | Giger et al. | |
| 2007/0276368 A1 | 11/2007 | Trieu et al. | |
| 2007/0276369 A1 | 11/2007 | Allard et al. | |
| 2007/0276378 A1 | 11/2007 | Harrison et al. | |
| 2007/0282196 A1 | 12/2007 | Birk et al. | |
| 2007/0288024 A1 | 12/2007 | Gollogly | |
| 2008/0027436 A1 | 1/2008 | Cournoyer et al. | |
| 2008/0033436 A1 | 2/2008 | Song et al. | |
| 2008/0048855 A1 | 2/2008 | Berger | |
| 2009/0030462 A1 | 1/2009 | Buttermann | |

FOREIGN PATENT DOCUMENTS

| | | | |
|---|---|---|---|
| FR | 2900563 A1 | 11/2007 | |
| FR | 2901991 A1 | 12/2007 | |
| WO | WO 99/51160 A1 | 10/1999 | |
| WO | WO 01/05463 A1 | 1/2001 | |
| WO | WO 2006/090380 A2 | 8/2006 | |
| WO | WO 2007/015239 A2 | 2/2007 | |
| WO | WO 2007/025191 A1 | 3/2007 | |
| WO | WO 2007/118179 A2 | 10/2007 | |
| WO | WO 2007/144489 A2 | 12/2007 | |
| WO | WO 2008/003952 A1 | 1/2008 | |
| WO | WO 2008/040880 A2 | 4/2008 | |

OTHER PUBLICATIONS

PCT Written Opinion of the International Searching Authority for PCT/US2009/060266, Applicant: Ellipse Technologies, Inc., Form PCT/ISA/237, dated Dec. 10, 2009 (5 pages).

Abe, J. Nagata, K., Ariyoshi, M., Inoue, A., "Experimental External Fixation Combined with Pecutaneous Discectomy in the Management of Scoliosis", Spine, 1999, vol. 24, No. 7, pp. 646-653, Lippincott Co., Philadelphia, U.S.A.

Buchowski, J., Bhatnagar, R., Skaggs, D., Sponseller, P., "Temporary Internal Distraction as an Aid to Correction of Severe Scoliosis", Journal of Bone and Joint Surgery American Edition, 2006, vol. 88A, No. 9, pp. 2035-2041, Journal of Bone and Joint Surgery, Boston, U.S.A.

Buchowski, J., Skaggs, D., Sponseller, P., "Temporary Internal Distraction as an Aid to Correction of Severe Scoliosis. Surgical Technique", Journal of Bone and Joint Surgery American Edition, 2007, vol. 89A No. Supp 2 (Pt. 2), pp. 297-309, Journal of Bone and Joint Surgery, Boston, U.S.A.

Burke, J. "Design of a Minimally Invasive Non Fusion Device for the Surgical Management of Scoliosis in the Skeletally Immature", Studies in Health Technology and Informatics, 2006, vol. 123, pp. 378-384, IOS Press, Amsterdam, The Netherlands.

Cole, J., Paley, D., Dahl, M., "Operative Technique. ISKD. Intramedullary Skeletal Kinetic Distractor. Tibial Surgical Technique" IS-0508(A)-OPT-US © Orthofix Inc. Nov. 2005.

Daniels, A., Gemperline, P., Grahn, A., Dunn, H., "A New Method for Continuous Intraoperative Measurement of Harrington Rod Loading Patterns", Annals of Biomedical Engineering, 1984, vol. 12, No. 3, pp. 233-246, Dordrecht Kluwer Academic/Plenum Publishers, New York, U.S.A.

Edelan, H., Eriksson, G., Dahlberg, E., "Instrument for distraction by limited surgery in scoliosis treatment", Journal of Biomedical Engineering, 1981, vol. 3, No. 2, pp. 143-146, Butterfield Scientific Limited, Guilford, England.

Hazem Elsebaie M.D., Single Growing Rods (Review of 21 cases). Changing the Foundations: Does it affect the Results?, J Child Orthop. (2007) 1:258.

Ember, T., Noordeen, H., "Distraction forces required during growth rod lengthening", Journal of Bone and Joint Surgery British Edition, 2006, vol. 88B, No. Supp II, p. 229, Churchill Livingstone, London, England.

Gao et al., CHD7 Gene Polymorphisms Are Associated with Susceptibility to Idiopathic Scoliosis, American Journal of Human Genetics, vol. 80, pp. 957-965 (May 2007).

Gebhart, M., Neel, M., Soubeiran, A., Dubousset, J., "Early clinical experience with a custom made growing endoprosthesis in children with malignant bone tumors of the lower extremity actioned by an external permanent magnet: the Phenix M system", International Society of Limb Salvage 14th International Symposium on Limb Salvage, Sep. 13, 2007, Hamburg, Germany.

Gillespie, R., O'Brien, J., "Harrington Instrumentation without Fusion", The Journal of Bone and Joint Surgery British Edition, 1981, vol. 63B, No. 3, p. 461, Churchill Livingstone, London, England.

Grass, P., Soto, A., Araya, H., "Intermittent Distracting Rod for Correction of High Neurologic Risk Congenital Scoliosis", Spine, 1997, vol. 22, No. 16, pp. 1922-1927, Lippincott Co., Philadelphia, U.S.A.

Grimer, R., Chotel, F., Abudu, S., Tillman, R., Carter, S., "Non-invasive extendable endoprosthesis for children—expensive but worth it", International Society of Limb Salvage 14th International Symposium on Limb Salvage, Sep. 13, 2007, Hamburg, Germany.

Guichet, J., Deromedis, B., Donnan, L., Peretti, G., Lascombes, P., Bado,F., "Gradual Femoral Lengthening with the Albizzia Intramedullary Nail", Journal of Bone and Joint Surgery American Edition, 2003, vol. 85, pp. 838-848. (12 pages).

Gupta, A., Meswania, J., Pollock, R., Cannon, S., Briggs, T., Taylor, S., Blunn, G., "Non-Invasive Distal Femoral Expandable Endoprosthesis for Limb-Salvage Surgery in Paediatric Tumours", The Journal of Bone and Joint Surgery British Edition, 2006, vol. 88-B, No. 5, pp. 649-654, Churchill Livingstone, London, England.

Hankemeier, S., Gösling, T., Pape, H., Wiebking, U., Krettek, C., "Limb Lengthening with the Intramedullary Skeletal Kinetic Distractor (ISKD)", Operative Orthopädie und Traumatologie, 2005, vol. 17, No. 1, pp. 79-101, Urban & Vogel, Munich, Germany.

Harrington, P., "Treatment of Scoliosis: Correction and Internal Fixation by Spine Instrumentation", The Journal of Bone and Joint Surgery American Edition, 1962, vol. 44A, No. 4, pp. 591-610, Journal of Bone and Joint Surgery, Boston, U.S.A.

Klemme, W., Denis, F., Winter, R., Lonstein, J., Koop, S., "Spinal Instrumentation without Fusion for Progressive Scoliosis in Young Children", Journal of Pediatric Orthopedics. 1997, vol. 17, No. 6, pp. 734-742, Raven Press, New York, U.S.A.

Lonner, B., "Emerging minimally invasive technologies for the management of scoliosis", Orthopedic Clinics of North America, 2007; vol. 38, No. 3, pp. 431-440, Saunders, Philadelphia, U.S.A.

Mineiro, J., Weinstein, S., "Subcutaneous Rodding for Progressive Spinal Curvatures: Early Results", Journal of Pediatric Orthopedics, 2002, vol. 22, No. 3, pp. 290-295, Raven Press, New York, U.S.A.

Moe, J., Kharrat, K., Winter, R., Cummine, J., "Harrington Instrumentation without Fusion Plus External Orthotic Support for the Treatment of Difficult Curvature Problems in Young Children", Clinical Orthopaedics and Related Research, 1984, No. 185. pp. 35-45, Lippincott Co., Philadelphia, U.S.A.

Nachemson, A., Elfstrom, G., "Intravital Wireless Telemetry of Axial Forces in Harrington Distraction Rods in Patients with Idiopathic Scoliosis", The Journal of Bone and Joint Surgery American Edition, 1971, vol. 53A, No. 3, pp. 445-465, Journal of Bone and Joint Surgery, Boston, U.S.A.

Nachlas, I., Borden, J., "The cure of experimental scoliosis by directed growth control". The Journal of Bone and Joint Surgery American Edition, 1951, vol. 33, No. A:1, pp. 24-34, Journal of Bone and Joint Surgery, Boston, U.S.A.

Newton, P., "Fusionless Scoliosis Correction by Anterolateral Tethering . . . Can it Work?", 39th Annual Scoliosis Research Society Meeting, Sep. 6, 2004, Buenos Aires, Argentina (transcript and slides supplied).

Rathjen, K, Wood, M., McClung, A., Vest, Z., "Clinical and Radiographic Results after Implant Removal in Idiopathic Scoliosis", Spine, 2007, vol. 32, No. 20, pp. 2184-2188, Lippincott Co., Philadelphia, U.S.A.

Reyes-Sanchez, A., Rosales, L., Miramontes, V., "External Fixation for Dynamic Correction of Severe Scoliosis", The Spine Journal, 2005, vol. 5, No. 4, pp. 418-426, Elsevier Science Inc., New York, U.S.A.

Rinsky, L., Gamble, J., Bleck, E., "Segmental Instrumentation Without fusion in Children with Progressive Scoliosis", Journal of Pediatric Orthopedics, 1985, vol. 5, No. 6, pp. 687-690, Raven Press, New York, U.S.A.

Schmerling, M., Wilkov, M., Sanders, A., "Using the Shape Recovery of Nitinol in the Harrington Rod Treatment of Scoliosis", Journal of Biomedical Materials Research, 1976, vol. 10, No. 6, pp. 879-892, Wiley, Hoboken, U.S.A.

Sharke, P., "The Machinery of Life", Mechanical Engineering Magazine, Feb. 2004, Printed from Internet site Oct. 24, 2007 http://www.memagazine.org/contents/current/features/moflife/moflife.html.

Smith J., "The Use of Growth-Sparing Instrumentation in Pediatric Spinal Deformity", Orthopedic Clinics of North America, 2007, vol. 38, No. 4, pp. 547-552, Saunders, Philadelphia, U.S.A.

Soubeiran, A., Gebhart, M., Miladi, L., Griffet, J., Neel, M., Dubousset, J., "The Phenix M System. A Mechanical Fully Implanted Lengthening Device Externally Controllable Through the Skin with a Palm Size Permanent Magnet; Applications to Pediatric Orthopaedics", 6th European Research Conference in Pediatric Orthopaedics, Oct. 6, 2006, Toulouse, France.

Soubeiran, A., Gebhart, M., Miladi, L., Griffet, J., Neel, M., Dubousset, J., "The Phenix M system, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany.

Takaso, M., Moriya, H., Kitahara, H., Minami, S., Takahashi, K., Isobe, K., Yamagata, M., Otsuka, Y., Nakata, Y., Inoue, M., "New remote-controlled growing-rod spinal instrumentation possibly applicable for scoliosis in young children", Journal of Orthopaedic Science, 1998, vol. 3, No. 6, pp. 336-340, Springer-Verlag, Tokyo, Japan.

Marco Teli, M.D. et al. Measurement of Forces Generated During Distraction of Growing Rods. Marco Teli, J. Child Orthop (2007) 1:257-258.

Tello C., "Harrington Instrumentation without Arthrodesis and Consecutive Distraction Program for Young Children with Sever Spinal Deformities: Experience and Technical Details", Orthopedic Clinics of North America, vol. 25, No. 2 1994. pp. 333-351. (19 pages).

Thompson, G., Akbarnia, B., Campbell, R., "Growing Rod Techniques in Early-Onset Scoliosis", Journal of Pediatric Orthopedics, 2007, vol. 27, No. 3, pp. 354-361, Raven Press, New York, U.S.A.

Thompson, G., Lenke, L., Akbarnia, B., McCarthy, R., Campbell, Jr., R., "Early Onset Scoliosis: Future Directions", 2007, Journal of Bone and Joint Surgery American Edition, vol. 89A, No. Supp 1, pp. 163-166, Journal of Bone and Joint Surgery, Boston, U.S.A.

Trias, A., Bourassa, P., Massoud, M., "Dynamic Loads Experienced in Correction of Idiopathic Scoliosis Using Two Types of Harrington Rods", Spine, 1979, vol. 4, No. 3, pp. 228-235, Lippincott Co., Philadelphia, U.S.A.

Verkerke, G., Koops, H., Veth, R., Oldhoff, J., Nielsen, H., vanden Kroonenberg, H., Grootenboer, H., van Krieken, F., "Design of a Lengthening Element for a Modular Femur Endoprosthetic System", Proceedings of the Institution of Mechanical Engineers Part H: Journal of Engineering in Medicine, 1989, vol. 203, No. 2, pp. 97-102, Mechanical Engineering Publications, London, England.

Verkerke, G., Koops, H., Veth, R., van den Kroonenberg, H., Grootenboer, H., Nielsen, H., Oldhoff, J., Postma, A., "An Extendable Modular Endoprosthetic System for Bone Tumour Management in the Leg", Journal of Biomedical Engineering, 1990, vol. 12, No. 2, pp. 91-96, Butterfield Scientific Limited, Guilford, England.

Verkerke, G., Koops, H., Veth, R., Grootenboer, H., De Boer, L., Oldhoff, J., Postma, A. "Development and Test of an Extendable Endoprosthesis for Bone Reconstruction in the Leg", The International Journal of Artificial Organs, 1994, vol. 17, No. 3, pp. 155-162, Wichtig Editore, Milan, Italy.

Wenger, H., "Spine Jack Operation in the Correction of Scoliotic Deformity", Archives of Surgery, 1961, vol. 83, pp. 123-132 (901-910), American Medical Association, Chicago, U.S.A.

White, A., Panjabi, M., "The Clinical Biomechanics of Scoliosis", Clinical Orthopaedics and Related Research, 1976, No. 118, pp. 100-112, Lippincott Co., Philadelphia, U.S.A.

* cited by examiner

EXTERNAL ADJUSTMENT DEVICE FOR DISTRACTION DEVICE

RELATED APPLICATIONS

This application claims priority to U.S. Provisional Patent Application No. 61/113,086 filed on Nov. 10, 2008 and U.S. Provisional Patent Application No. 61/240,071 field on Sep. 4, 2009. The '086 and '071 Provisional patent applications are incorporated by reference as if set forth fully herein.

FIELD OF THE INVENTION

The field of the invention generally relates to medical devices for treating disorders of the skeletal system.

BACKGROUND

Scoliosis is a general term for the sideways (lateral) curving of the spine, usually in the thoracic or thoracolumbar region. Scoliosis is commonly broken up into different treatment groups, Adolescent Idiopathic Scoliosis, Early Onset Scoliosis and Adult Scoliosis.

Adolescent Idiopathic Scoliosis (AIS) typically affects children between ages 10 and 16, and becomes most severe during growth spurts that occur as the body is developing. One to two percent of children between ages 10 and 16 have some amount of scoliosis. Of every 1000 children, two to five develop curves that are serious enough to require treatment. The degree of scoliosis is typically described by the Cobb angle, which is determined, usually from x-ray images, by taking the most tilted vertebrae above and below the apex of the curved portion and measuring the angle between intersecting lines drawn perpendicular to the top of the top vertebrae and the bottom of the bottom. The term idiopathic refers to the fact that the exact cause of this curvature is unknown. Some have speculated that scoliosis occurs when, during rapid growth phases, the ligamentum flavum of the spine is too tight and hinders symmetric growth of the spine. For example, as the anterior portion of the spine elongates faster than the posterior portion, the thoracic spine begins to straighten, until it curves laterally, often with an accompanying rotation. In more severe cases, this rotation actually creates a noticeable deformity, wherein one shoulder is lower than the other. Currently, many school districts perform external visual assessment of spines, for example in all fifth grade students. For those students in whom an "S" shape or "C" shape is identified, instead of an "I" shape, a recommendation is given to have the spine examined by a physician, and commonly followed-up with periodic spinal x-rays.

Typically, patients with a Cobb angle of 20° or less are not treated, but are continually followed up, often with subsequent x-rays. Patients with a Cobb angle of 40° or greater are usually recommended for fusion surgery. It should be noted that many patients do not receive this spinal assessment, for numerous reasons. Many school districts do not perform this assessment, and many children do not regularly visit a physician, so often, the curve progresses rapidly and severely. There is a large population of grown adults with untreated scoliosis, in extreme cases with a Cobb angle as high as or greater than 90°. Many of these adults, though, do not have pain associated with this deformity, and live relatively normal lives, though oftentimes with restricted mobility and motion. In AIS, the ratio of females to males for curves under 10° is about one to one, however, at angles above 30°, females outnumber males by as much as eight to one. Fusion surgery can be performed on the AIS patients or on adult scoliosis patients. In a typical posterior fusion surgery, an incision is made down the length of the back and Titanium or stainless steel straightening rods are placed along the curved portion. These rods are typically secured to the vertebral bodies, for example with hooks or bone screws, or more specifically pedicle screws, in a manner that allows the spine to be straightened. Usually, at the section desired for fusion, the intervertebral disks are removed and bone graft material is placed to create the fusion. If this is autologous material, the bone is harvested from a hip via a separate incision.

Alternatively, the fusion surgery may be performed anteriorly. A lateral and anterior incision is made for access. Usually, one of the lungs is deflated in order to allow access to the spine from this anterior approach. In a less-invasive version of the anterior procedure, instead of the single long incision, approximately five incisions, each about three to four cm long are made in several of the intercostal spaces (between the ribs) on one side of the patient. In one version of this minimally invasive surgery, tethers and bone screws are placed and are secured to the vertebra on the anterior convex portion of the curve. Currently, clinical trials are being performed which use staples in place of the tether/screw combination. One advantage of this surgery in comparison with the posterior approach is that the scars from the incisions are not as dramatic, though they are still located in a visible area, when a bathing suit, for example, is worn. The staples have had some difficulty in the clinical trials. The staples tend to pull out of the bone when a critical stress level is reached.

In some cases, after surgery, the patient will wear a protective brace for a few months as the fusing process occurs. Once the patient reaches spinal maturity, it is difficult to remove the rods and associated hardware in a subsequent surgery, because the fusion of the vertebra usually incorporates the rods themselves. Standard practice is to leave this implant in for life. With either of these two surgical methods, after fusion, the patient's spine is now straight, but depending on how many vertebra were fused, there are often limitations in the degree of flexibility, both in bending and twisting. As these fused patients mature, the fused section can impart large stresses on the adjacent non-fused vertebra, and often, other problems including pain can occur in these areas, sometimes necessitating further surgery. This tends to be in the lumbar portion of the spine that is prone to problems in aging patients. Many physicians are now interested in fusionless surgery for scoliosis, which may be able to eliminate some of the drawbacks of fusion.

One group of patients in which the spine is especially dynamic is the subset known as Early Onset Scoliosis (EOS), which typically occurs in children before the age of five, and more often in boys than in girls. This is a more rare condition, occurring in only about one or two out of 10,000 children, but can be severe, sometimes affecting the normal development of organs. Because of the fact that the spines of these children will still grow a large amount after treatment, non-fusion distraction devices known as growing rods and a device known as the VEPTR—Vertical Expandable Prosthetic Titanium Rib ("Titanium Rib") have been developed. These devices are typically adjusted approximately every six months, to match the child's growth, until the child is at least eight years old, sometimes until they are 15 years old. Each adjustment requires a surgical incision to access the adjustable portion of the device. Because the patients may receive the device at an age as early as six months old, this treatment requires a large number of surgeries. Because of the multiple surgeries, these patients have a rather high preponderance of infection.

Returning to the AIS patients, the treatment methodology for those with a Cobb angle between 20° and 40° is quite controversial. Many physicians proscribe a brace (for example, the Boston Brace), that the patient must wear on their body and under their clothes 18 to 23 hours a day until they become skeletally mature, for example to age 16. Because these patients are all passing through their socially demanding adolescent years, it is quite a serious prospect to be forced with the choice of either wearing a somewhat bulky brace that covers most of the upper body, having fusion surgery that may leave large scars and also limit motion, or doing nothing and running the risk of becoming disfigured and possibly disabled. It is commonly known that many patients have at times hidden their braces, for example, in a bush outside of school, in order to escape any related embarrassment. The patient compliance with brace wearing has been so problematic that there have been special braces constructed which sense the body of the patient, and keep track of the amount of time per day that the brace is worn. Patients have even been known to place objects into unworn braces of this type in order to fool the sensor. Coupled with the inconsistent patient compliance with brace usage, is a feeling by many physicians that braces, even if used properly, are not at all effective at curing scoliosis. These physicians may agree that bracing can possibly slow down or even temporarily stop curve (Cobb angle) progression, but they have noted that as soon as the treatment period ends and the brace is no longer worn, often the scoliosis rapidly progresses, to a Cobb angle even more severe than it was at the beginning of treatment. Some say the reason for the supposed ineffectiveness of the brace is that it works only on a portion of the torso, and not on the entire spine. Currently a prospective, randomized 500 patient clinical trial known as BrAIST (Bracing in Adolescent Idiopathic Scoliosis Trial) is enrolling patients, 50% of whom will be treated with the brace and 50% of who will simply be watched. The Cobb angle data will be measured continually up until skeletal maturity, or until a Cobb angle of 50° is reached, at which time the patient will likely undergo surgery. Many physicians feel that the BrAIST trial will show that braces are completely ineffective. If this is the case, the quandary about what to do with AIS patients who have a Cobb angle of between 20° and 40° will only become more pronounced. It should be noted that the "20° to 40°" patient population is as much as ten times larger than the "40° and greater" patient population.

SUMMARY

In a first embodiment, an external adjustment device includes a support member and first and second cylindrical magnets disposed within a cover and mounted on one side of the support member, the first and second cylindrical magnets mounted on respective shafts passing through the support member and terminating at respective first and second gears disposed on an opposing side of the support member. The external adjustment device includes a pair of handles secured to the support member. A motor is mounted to the support member on a side opposite the first and second cylindrical magnets, the motor configured in a geared arrangement with the first and second gears. The external adjustment device further includes a display configured to visually display information to a user of the external adjustment device.

In a second embodiment, a system includes an external adjustment device and a magnetically shielded storage case. The external adjustment device includes an external adjustment device comprising first and second cylindrical magnets disposed within a cover, the first and second cylindrical magnets rotationally mounted on respective shafts. The external adjustment device also includes a pair of handles, a motor configured to rotate the first and second cylindrical magnets, and a display configured to visually display information to a user of the external adjustment device. The external adjustment device can be stored in a storage case. The storage case may at least partially cover the first and second cylindrical magnets. The storage case may optionally be formed from a material that provides magnetic shielding.

In another embodiment, a method of positioning an external adjustment device relative to a patient having an implanted magnetic assembly includes placing a magnetic viewing sheet adjacent to a patient; identifying the location of an implanted magnetic assembly using the magnetic viewing sheet by visualizing a magnetic image of the implanted magnetic assembly in the magnetic viewing sheet; and placing the external adjustment device on the patient adjacent to the location where the magnetic image was located.

In yet another embodiment, a method of confirming the location of an implanted magnetic assembly includes identifying the general region of the patient where the implanted magnetic assembly is believed to be located; providing an external locating magnet in close proximity to the general region; and moving the external locating magnet around to find the location where the magnetic force is the strongest.

In still another embodiment, a method of confirming the location of an implanted magnetic assembly includes identifying the general region of the patient where the implanted magnetic assembly is believed to be located. An external adjustment device is moved adjacent to the patient in the general region, the external adjustment device comprising a support member having first and second cylindrical magnets disposed on one side thereof and a pair of handles disposed on an opposing side thereof along with a motor configured to rotate the first and second cylindrical magnets, wherein a center of mass of the external adjustment device is located substantially at a base of the pair of handles adjacent to the support member. The location of the implanted magnetic assembly is sensed by detecting magnetic attraction of the external adjustment device toward the patient.

In still another embodiment, an external adjustment device includes a support member having first and second cylindrical magnets disposed on a first side thereof and a pair of handles disposed on an opposing, second side of the support member. A motor is disposed on the second side of the support member and configured to rotate the first and second cylindrical magnets. A microcontroller is disposed on or in the external adjustment device, the microcontroller having contained therein instructions for preventing one or more device operations.

In still another embodiment, a method of confirming the location of an implanted magnetic assembly includes identifying the general region of the patient where the implanted magnetic assembly is believed to be located and moving an external adjustment device adjacent to the patient in the general region. The external adjustment device includes a support member having first and second cylindrical magnets disposed on one side thereof and separated by a viewing aperture interposed there between, the external adjustment device further comprising a pair of handles disposed on an opposing side thereof along with a motor configured to rotate the first and second cylindrical magnets. The location of the implanted magnetic assembly is identified by moving the external adjustment device in the general region and at least partially viewing the general region through the viewing aperture to identify a lump.

DETAILED DESCRIPTION OF THE ILLUSTRATED EMBODIMENTS

Figure 1:
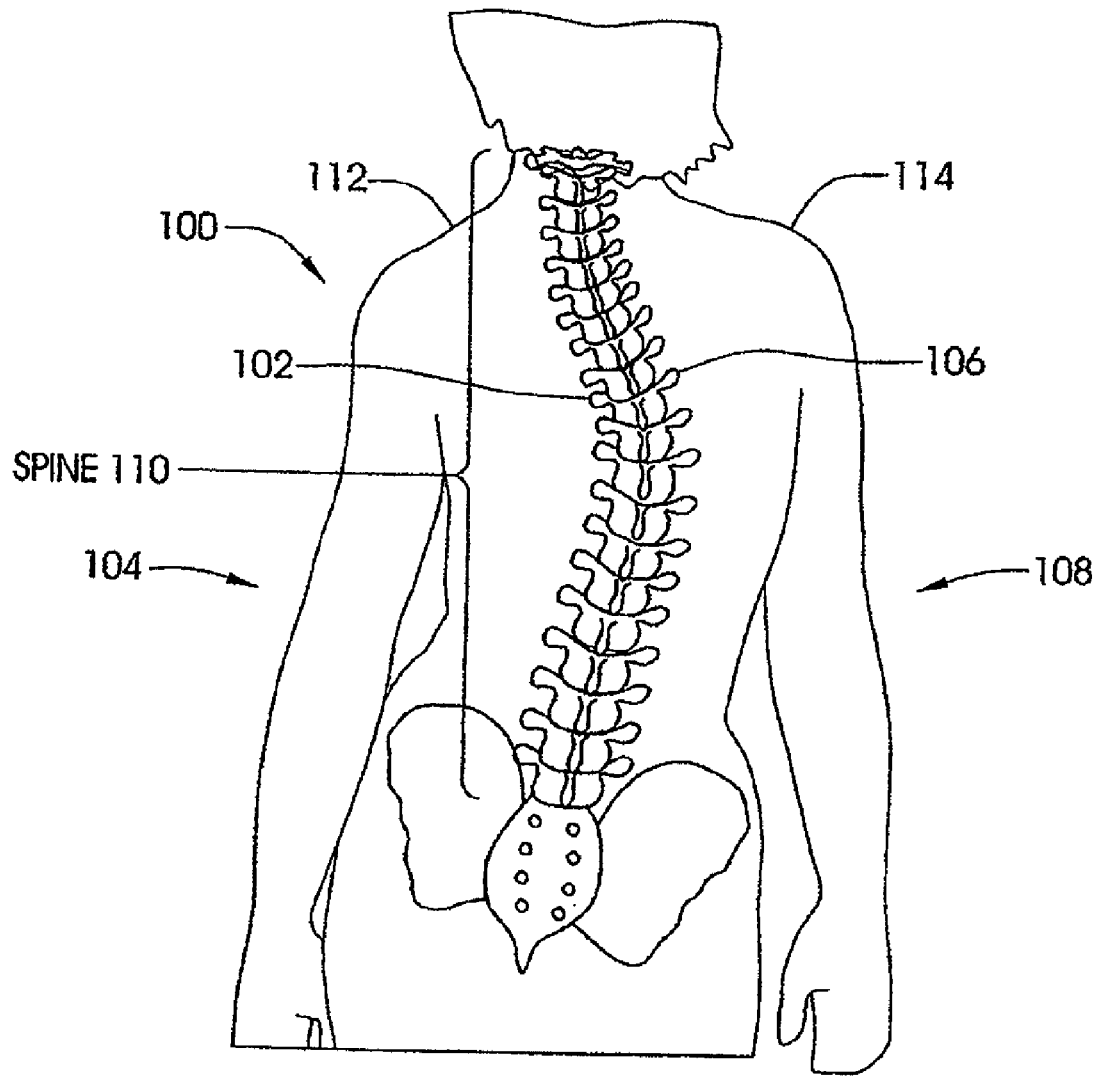
FIG. 1 illustrates the spine of a person with scoliosis.

FIG. 1 illustrates a patient 100 with scoliosis. The patient 100 may be a human being or mammalian animal. The concave portion 102 of the spinal curve can be seen on the left side 104 of the patient 100, and the convex portion 106 can be seen on the right side 108 of the patient 100. Of course, in other patients, the concave portion 102 may appear on the right side 108 of the patient 100 while the convex portion 106 may be found on the left side 104 of the patient. In addition, as seen in FIG. 1, some rotation of the spine 110 is present, and unevenness between the left shoulder 112 and right shoulder 114 is seen.

Figure 2:
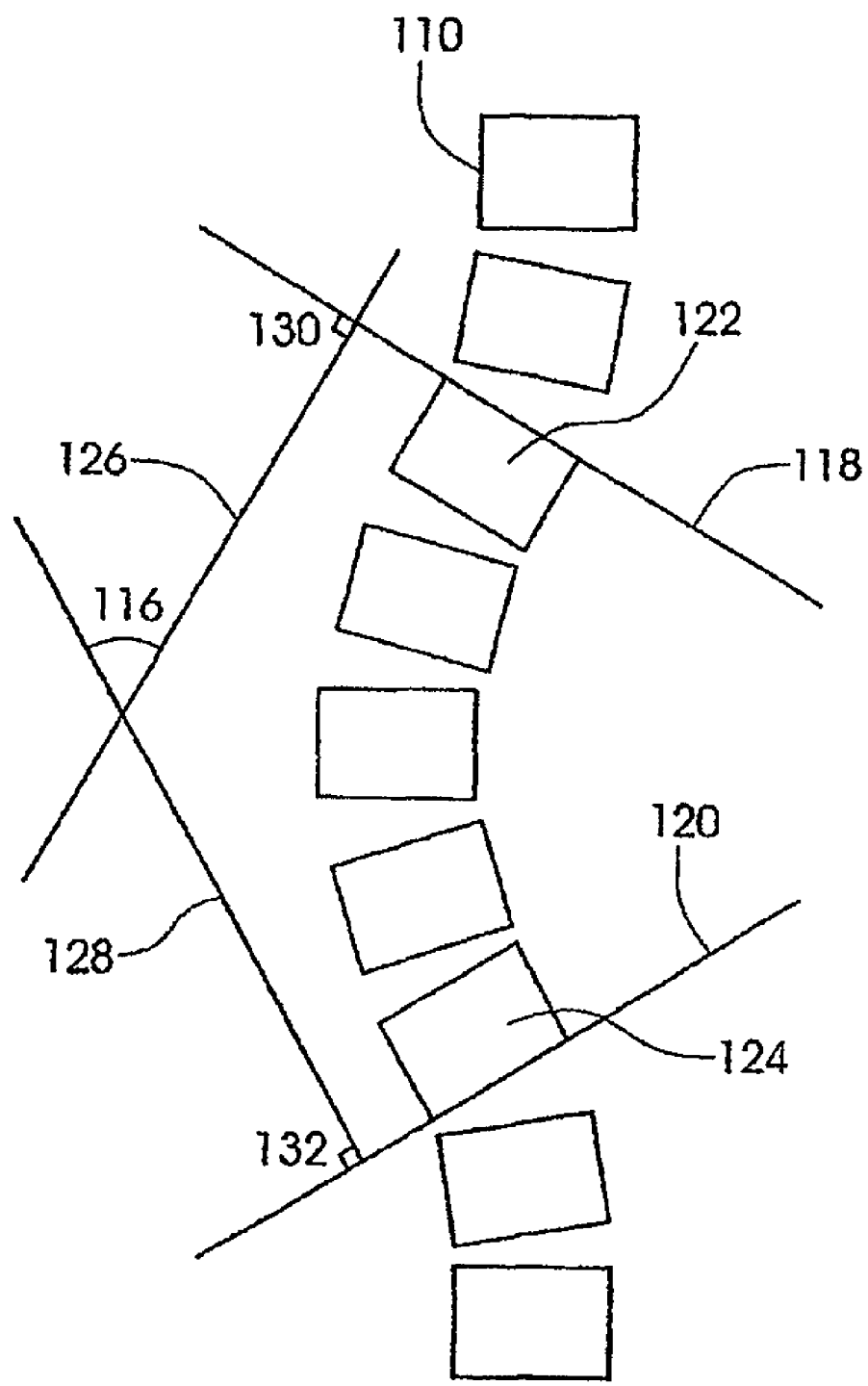
FIG. 2 illustrates the Cobb angle of a scoliotic spine.

FIG. 2 illustrates the Cobb angle 116 of a spine 110 of a patient with scoliosis. To determine the Cobb angle, lines 118 and 120 are drawn from vertebra 122 and 124, respectively. Intersecting perpendicular lines 126 and 128 are drawn by creating 90° angles 130 and 132 from lines 118 and 120. The angle 116 created from the crossing of the perpendicular lines 126 and 128 is defined as the Cobb angle. In a perfectly straight spine, this angle is 0°.

Figure 3:
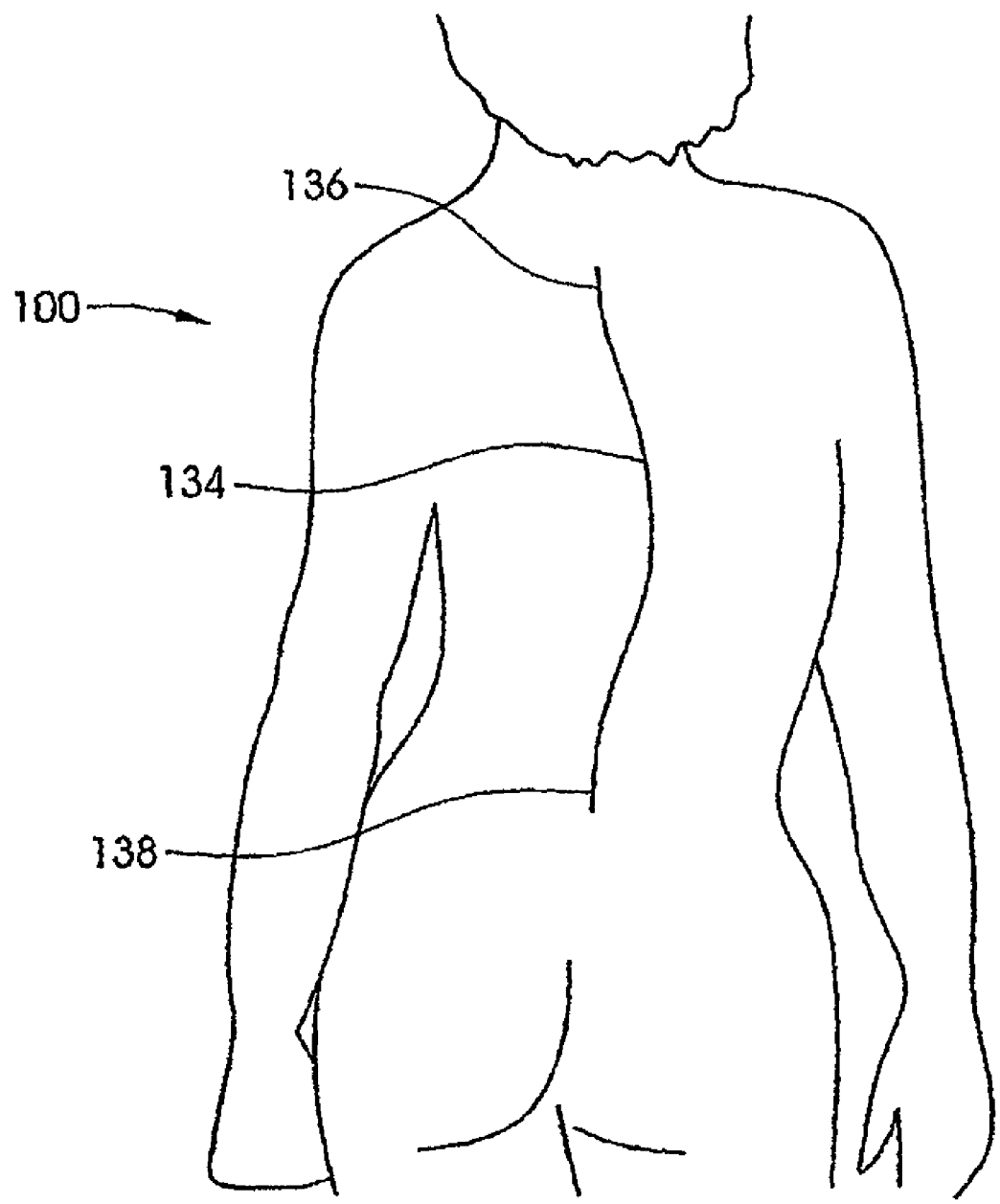
FIG. 3 illustrates the large incision made during prior art scoliosis fusion surgery.

In many Adolescent Idiopathic Scoliosis (AIS) patients with a Cobb angle of 40° or greater, spinal fusion surgery is typically the first option. FIG. 3 illustrates a long incision 134 formed in the patient 100 which is typically made during posterior scoliosis fusion surgery. This type of fusion surgery is known in the prior art. The long incision 134 extends between an upper end 136 and a lower end 138. The length of this incision 134 is longer than the length of the section of the vertebra to be fused. The actual length between the upper end 136 and the lower end 138 varies, depending on the size of the patient, and the extent of the scoliosis, but in AIS patients this length is significantly longer than 15 cm. More typically, it is longer than 25 cm.

Figure 4:
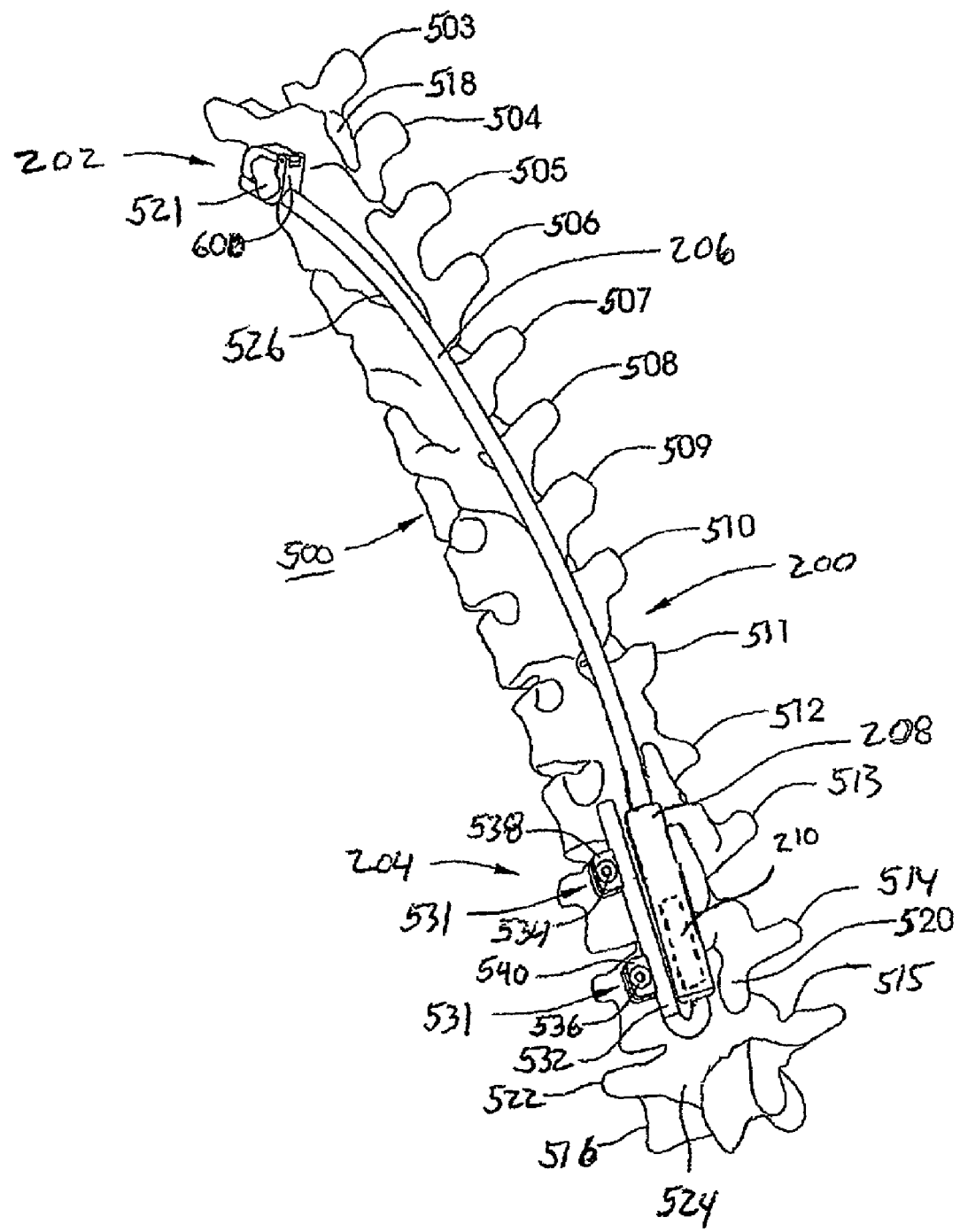
FIG. 4 illustrates an exemplary distraction device mounted on the spine of a patient.

FIG. 4 illustrates a distraction device 200 for treating scoliosis according to one embodiment. The distraction device 200, which is an implantable device, is fixated at its upper end 202 and lower end 204 to the patient's spine 500. The illustrated example of the spine 500 includes the particular thoracic and lumbar vertebrae that typically encompass a scoliotic curve, for example the curve of a patient with adolescent idiopathic scoliosis. The T3 through T12 thoracic vertebrae, 503, 504, 505, 506, 507, 508, 509, 510, 511, 512, respectively and the L1 through L3 vertebrae, 513, 514, 515 are depicted in FIG. 4, not in a severe scoliotic condition, but in a very slight residual curve that represents a modest curve that has been partially or completely straightened during the implantation procedure.

Each vertebra is different from the other vertebra by its size and shape, with the upper vertebra generally being smaller than the lower vertebra. However, generally, the vertebrae have a similar structure and include a vertebral body 516, a spinous process 518, 520, laminae 526, transverse processes 521, 522 and pedicles 524. In this embodiment, the distraction device 200 includes a distraction rod 206 which is adjustable (lengthwise) via a coupled adjustable portion 208. The distraction device 200 is fixated to the spine 500 via a clamp 600 at the upper end 202 of the distraction rod 206. In FIG. 4, the clamp 600 is secured around the transverse process 521 of the T4 vertebra 504. Alternatively, the clamp 600 may be secured around an adjacent rib (not shown) or rib facet. In still another alternative, the clamp may be replaced by a laminar and pedicle hook system, or pedicle screw system. Exemplary pedicle hook systems or pedicle screw systems may be found in U.S. patent application Ser. Nos. 12/121,355 and 12/250,442 which are incorporated by reference as if set forth fully herein.

Referring back to FIG. 4, the distraction device 200 is illustrated as being fixated to the spine 500 with a pedicle screw system 531 comprising a connecting rod 532 and two toe clamps 538, 540. The connecting rod 532 is shown curving back on itself in the shape of a "J." The connecting rod 532 then interfaces with the adjustable portion 208. The adjustable portion 208 of the distraction device 200 contains a magnetic assembly 210 (illustrated in dashed lines) having a permanent magnet configured to drive a lead screw that, depending on the direction of rotation of the internal magnet, will extend or retract the distraction rod 206 using the adjustable portion 208. Lengthening of the distraction rod 206, for example, will impart a distraction force to the spine 500. Retracting the distraction rod 206 will lower or remove the distraction force on the spine 500, for example if too high a distraction force causes pain or complications. It may even be desired to use the device to compress the spine or bone, for example at an anterior portion of the spine or at the convex portion of a curve. Examples of various magnetic assemblies 210 for use in distraction devices 200 may be found in U.S. patent application Ser. No. 12/121,355 and 12/250,442.

Still referring to FIG. 4, a locking screw 534 can be loosened to adjust the angle of the connecting rod 532 into the desired orientation and then locking screw 534 can be tightened so that toe clamp 538 securely holds connecting rod 532 in place without further rotation. The second toe clamp 540 is adjusted in the same way, by tightening locking screw 536. Because a scoliotic spine is also rotated (usually the center section is rotated to the right in AIS patients), the non-fusion embodiment presented here allows de-rotation of the spine 500 to happen naturally, because there is no fixation at the middle portion of the distraction device 200.

In order to further facilitate this de-rotation, the distraction device 200 may allow for free rotation at its ends. For example, the adjustable portion 208 may be coupled to the connecting rod 532 via an articulating joint. U.S. patent application Ser. Nos. 12/121,355 and 12/250,442 describe various articulating interfaces and joints that may be utilized to couple the adjustable portion 108 to the connecting rod 532 or the like.

It should be noted that distraction rod 206 may be pre-curved with the typical shape of a normal saggital spine, but it should also be noted that the curve may be slightly different than standard scoliosis fusion instrumentation, because in the non-fusion embodiment described herein, the distraction device 200 is not flush with the spine but rather is placed either subcutaneous or sub-fascial, and thus is not below the back muscles. The only portions of the distraction device 200 that are designed to be placed below the muscles are the clamp 600 and the portion of the distraction rod 206 immediately adjacent the clamp 600, the pedicle screw system 531 and the connecting rod 532. Thus, FIG. 4 illustrates an embodiment in which the bulk of the hardware associated with the distraction device 200 is placed over the muscle. It should be understood, however, that in alternative configurations, any other part of the entire implantable embodiment may be placed under the muscle (i.e., sub-muscular). It should be appreciated that a much smaller amount of muscle needs to be dissected during the procedure in comparison with current fusion procedures. This will allow for a much shorter procedure, much less blood loss, much quicker recovery, and less time in the hospital/less risk of infection. Further, it may be desirable to produce the "J" curve of the connecting rod 532 or any other curve at the connecting rod 532 with optional flanges or ribs at their highest stress points in order to increase their durability in demanding implant conditions.

Figure 5:
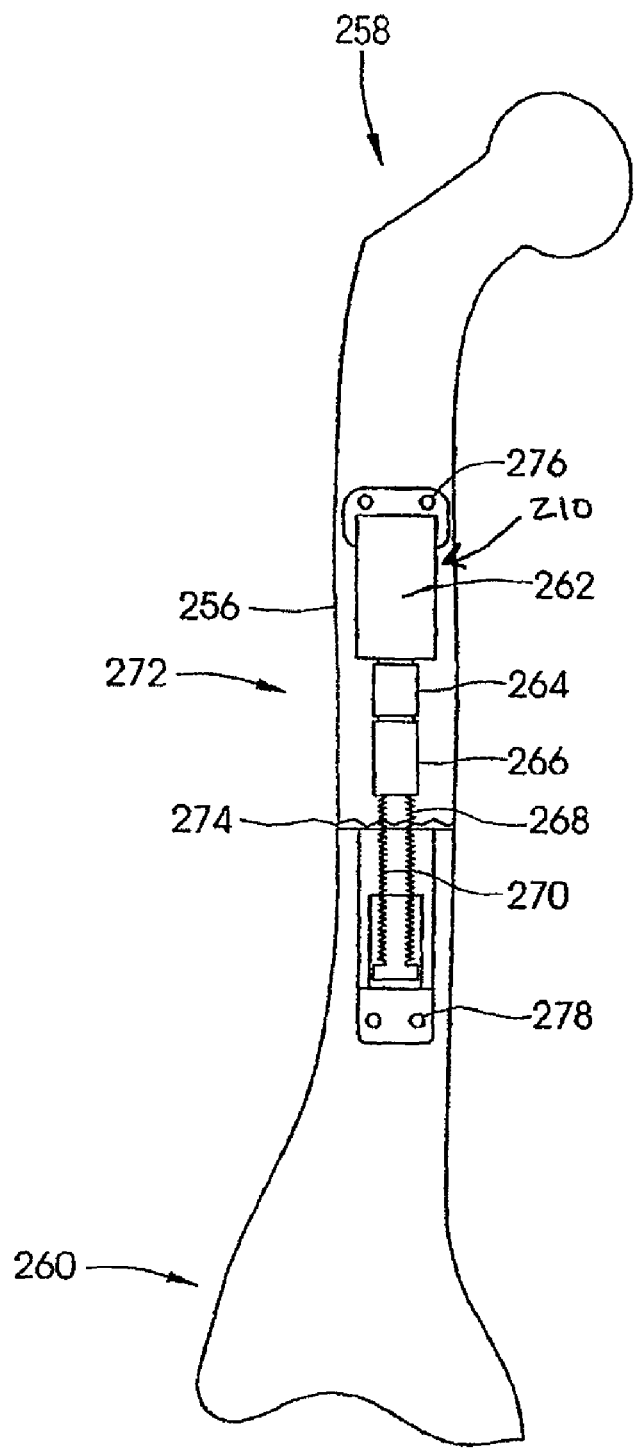
FIG. 5 illustrates another exemplary distraction device mounted in a bone of a patient.

FIG. 5 illustrates a bone growth distraction device 272 that is attached to bone 256 having a proximal portion 258 and a distal portion 260 by a proximal securement member 276 and a distal securement member 278. The securement members 276, 278 may operate using any number of securement devices or methods known to attach a device to bone, including screws, clamps or even adhesive materials. In cases of a bone fracture, a fracture site 274 is illustrated, though it should be noted that this fracture is not always present in some of the applications. As seen in FIG. 5, the bone growth distraction device 272 includes a magnetic assembly 210 that includes a cylindrical magnet 262 that is configured to rotate on its axis in response to an externally applied magnetic field. Rotation of the cylindrical magnet 262 effectuates rotation of a planetary gear set 266. An optional slip clutch 264 is illustrated as being disposed between the cylindrical magnet 262 and the planetary gear set 266, though slip clutch 264 may be disposed at any other location along the drive transmission. Rotation of the planetary gear set 266 in a first direction (e.g., either clockwise or counter-clockwise depending on configuration) causes lead screw 268 to turn within internal thread 270 causing distraction (e.g., elongation) of the bone 256. Bone growth distraction device 272 may be implanted in a single operation. Subsequent adjustments are performed non-invasively, and if desired can be performed frequently in order to precisely control bone growth. An exemplary daily adjustment in bone distraction is 1 mm. An adjustment device such as external adjustment device 700 described herein may be used to rotate the cylindrical magnet 262. An external adjustment device 700 of the type described herein may also be used to distract and retract the distraction device 200 illustrated in FIG. 4 by magnetic coupling to its magnetic assembly 210.

FIGS. 6-12 illustrate various views of an external adjustment device 700. The external adjustment device 700 is configured to remotely drive and control the magnetic assembly 210 of the distraction devices (e.g., distraction devices 200, 272). The external adjustment device 700 includes a left handle 702 and a right handle 704 that are affixed to a support member 730. In one particular aspect, the support member 730 may take the form of a base or plate. The handles 702, 704 permit a user to hold and manipulate the external adjustment device 700. The external adjustment device 700 includes two external magnets 706, 708 located on an opposing side of the support member 730. The two external magnets 706, 708 may be housed within a cover or casing as illustrated by cover 746 in FIG. 12. In this regard, the magnets 706, 708 are able to rotate within the cover 746 that separates the magnets 706, 708 from the external environment. Preferably, the cover 746 is rigid and relatively thin walled at least at the portion directly covering the permanent magnets 706, 708, in order to minimize the gap between the permanent magnets 706, 708 and the magnetic assembly 210. The two external magnets 706, 708 may be made from rare earth magnets such as, for instance, Neodymium-Iron-Boron (NdFeB) although other rare earth magnets are also possible. Each magnet 706, 708 may have a length of around 1.5 inches and a diameter of around 1.0 to 3.5 inches. Both magnets 706, 708 are diametrically magnetized (poles are perpendicular the long axis of each permanent magnet 706, 708).

The external adjustment device 700 includes a motor 705 that is contained within a motor cover 712. Optionally, a power cord 711 is operatively coupled to the motor 705 to provide a source of power. The power source may include a direct current (DC) source or it may include an alternating current (AC) source. The external adjustment device 700 may even operate primarily on one source (e.g., AC) but have the ability to switch to a back-up power source (e.g., DC batteries) in the event of a power failure or other interruption.

The external adjustment device 700 includes two push buttons 722, 724. Distraction button 722 is operated with the right thumb, for example, while still holding the right handle 704, and causes the external magnets 706, 708 to turn in the direction that causes distraction of the implanted distraction device. Distraction button 722 is optionally labeled with distraction symbol 717. Retraction button 724 is operated with the left thumb, for example while still holding the left handle 702, and causes the external magnets 706, 708 to turn in the opposite direction, that causing retraction of the implanted distraction device. Retraction button 724 is optionally labeled with retraction symbol 719. For example, if too much distraction is applied, the retraction button 724 may be pushed to reverse the undesired amount of distraction. The motor 705 may rotate the magnets 706, 708 at a faster speed, for example, when in retraction mode than in distraction mode, so that the distraction operation may be more precise, and the retraction (for example during an emergency situation) may be more immediate. The difference in speeds may be achieved by a multi-speed motor 705 or by gearing and the like. It may be desired that if both of the buttons 722, 724 are pressed at the same time, the external adjustment device 700 shuts off or does not operate.

As seen in FIGS. 6, 7, and 10-12, a display 715 is provided on the external adjustment device 700 which allows the user to visualize information, such as the current state of the distraction device 200, 272, the amount of distraction length desired or achieved, the rate of change of the distraction length, the rotational speed of the cylindrical magnets 706, 708, or distraction force. The display 715 advantageously provides information feedback to the user prior to, during, or after adjusting the particular distraction device within the patient 100. The display 715 may also be coupled with an auditory or even tactile cue (e.g., vibrations) to add further functionality.

Figure 6:
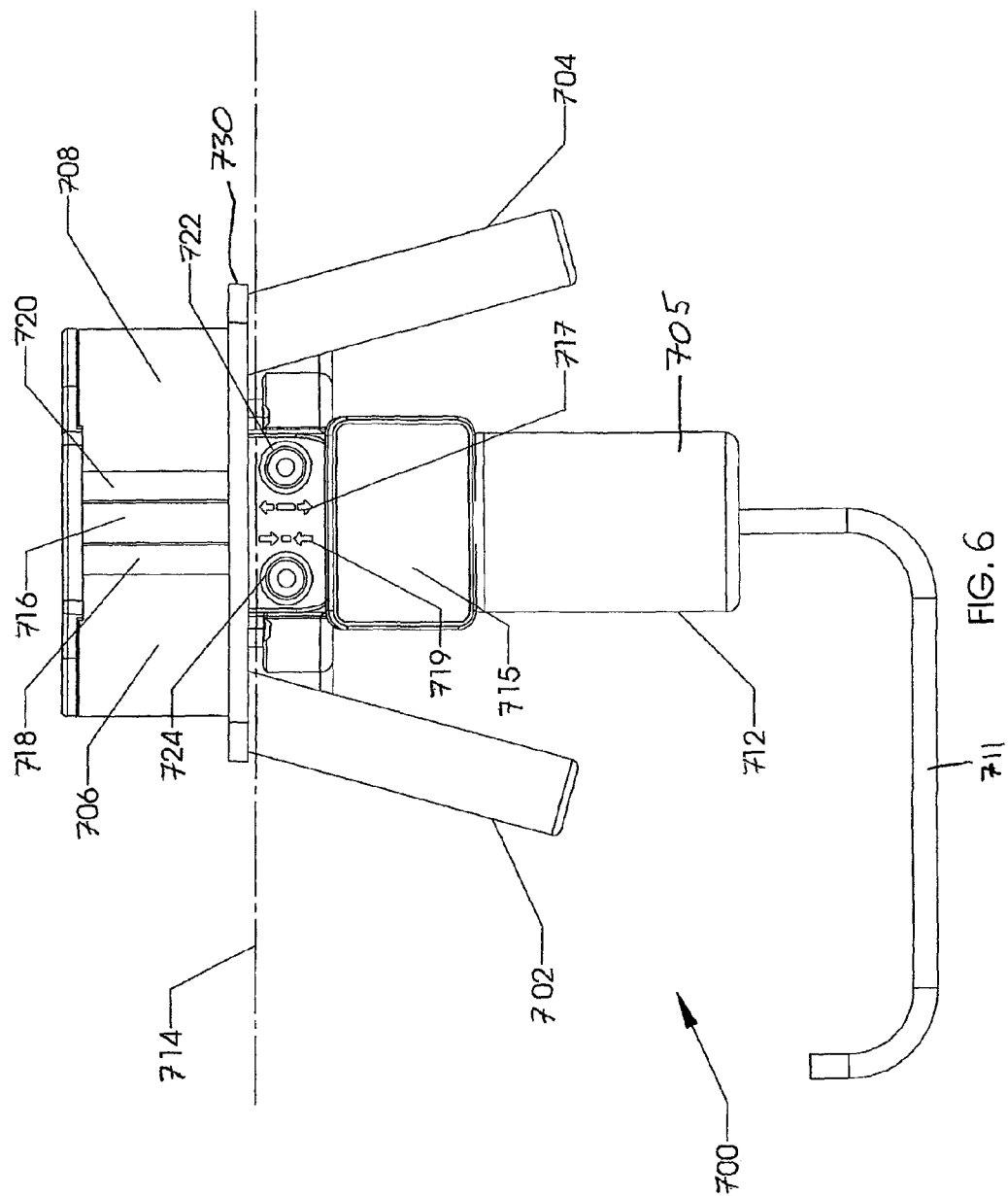
FIG. 6 is a top plan view of an external adjustment device according to one embodiment.
Figure 7:
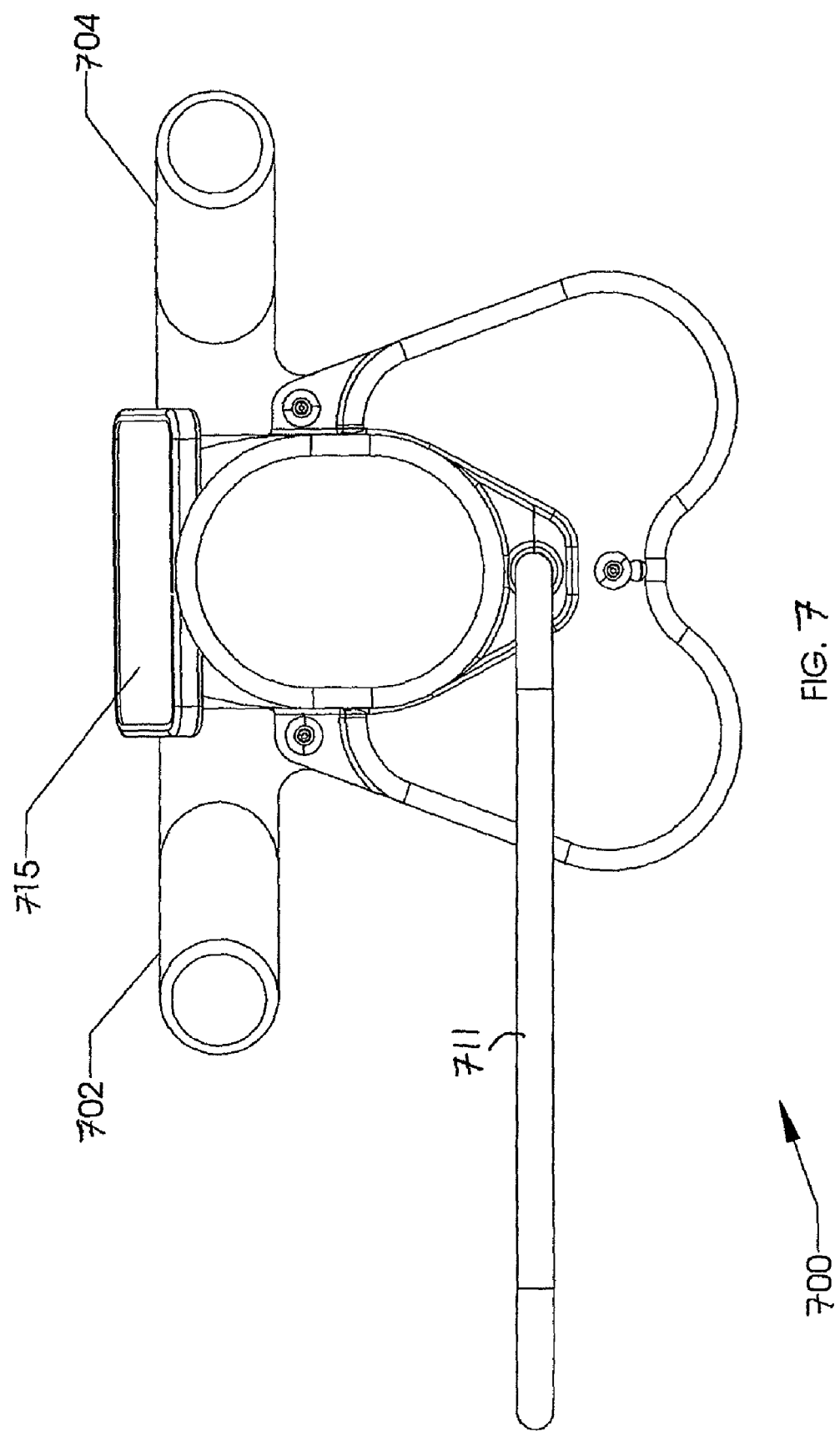
FIG. 7 is a rear view of the external adjustment device of FIG. 6.
Figure 8:
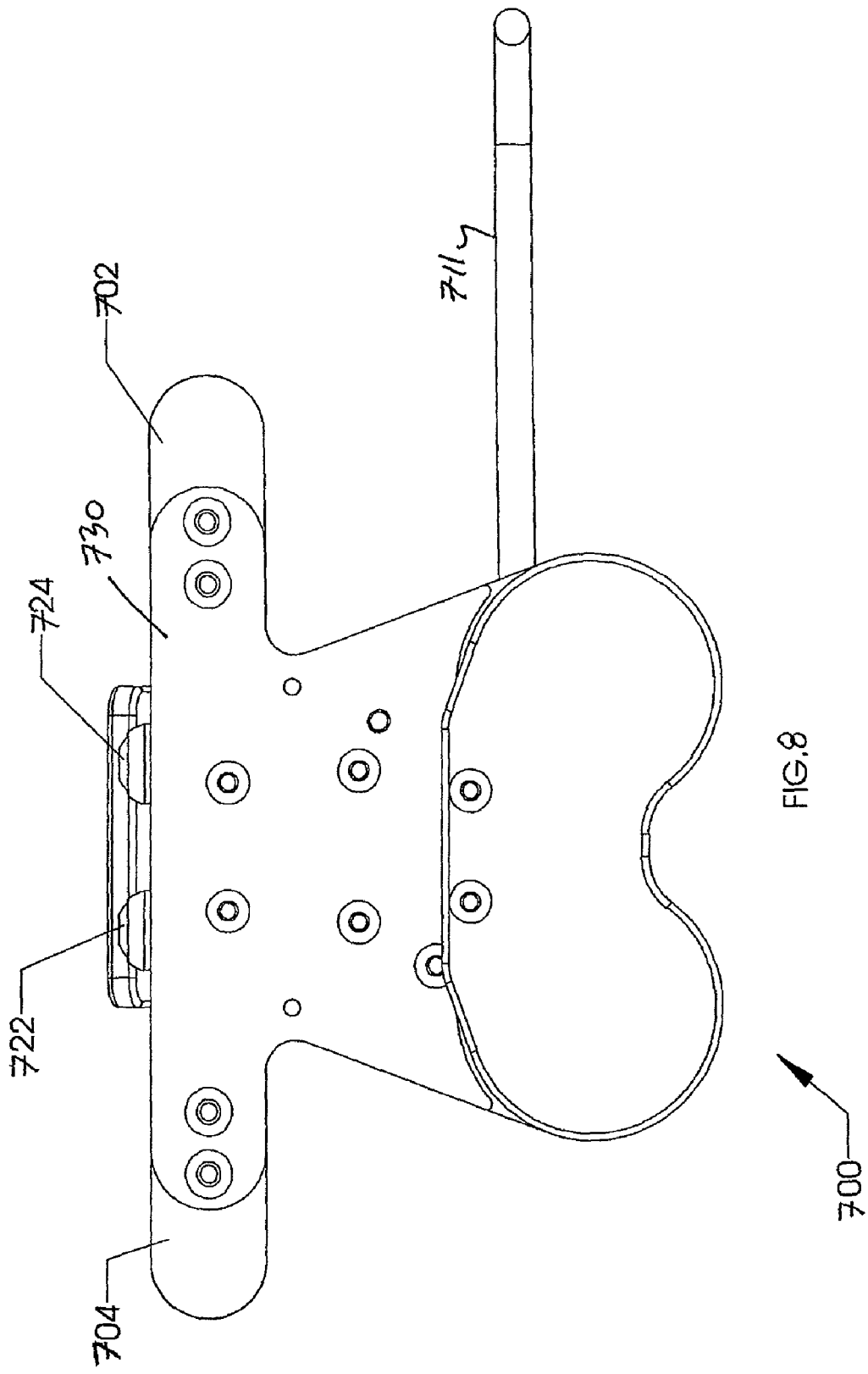
FIG. 8 is a front view of the external adjustment device of FIG. 6.
Figure 9:
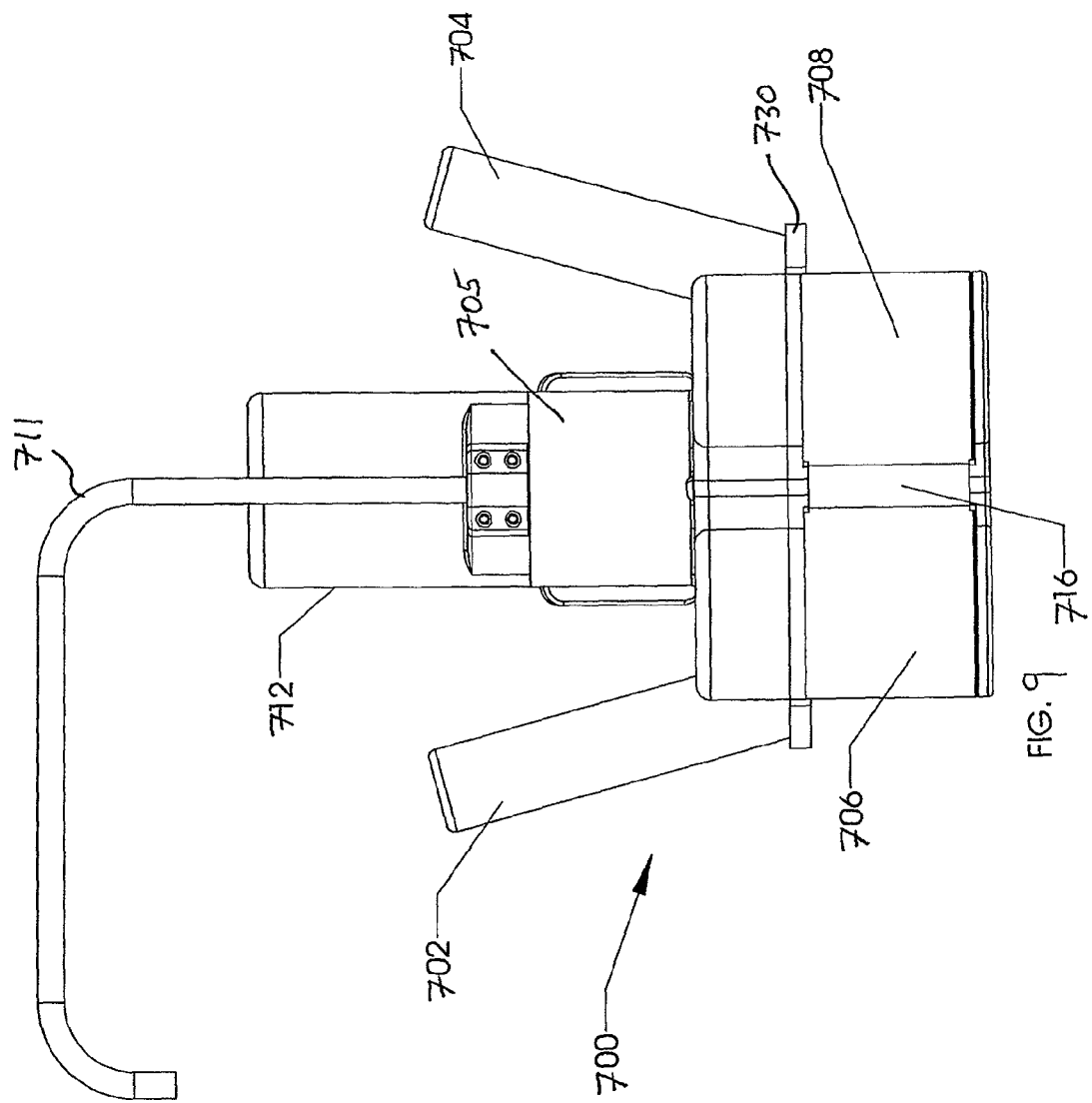
FIG. 9 is a bottom plan view of the external adjustment device of FIG. 6.
Figure 10:
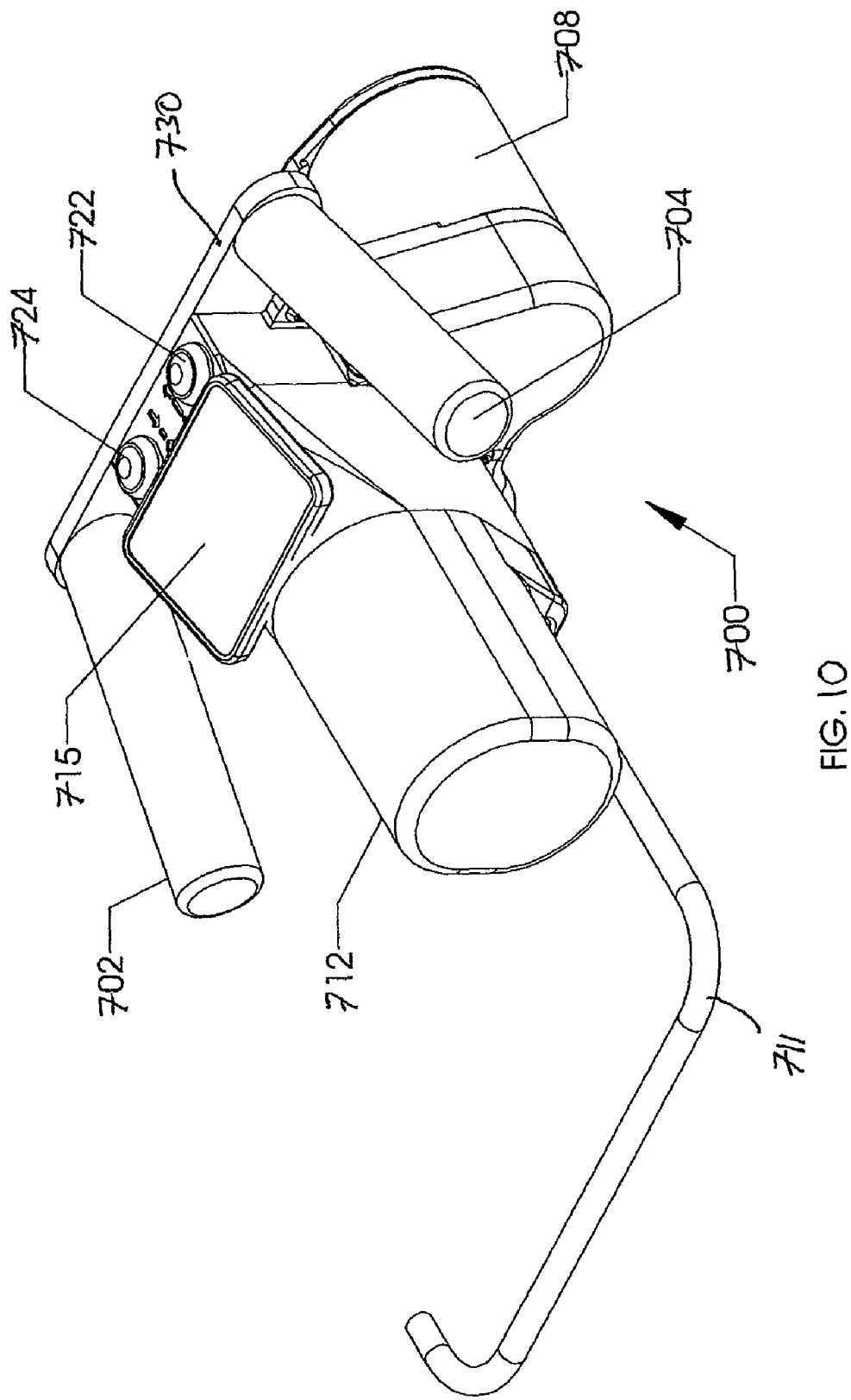
FIG. 10 is a perspective view of the external adjustment device of FIG. 6.
Figure 11:
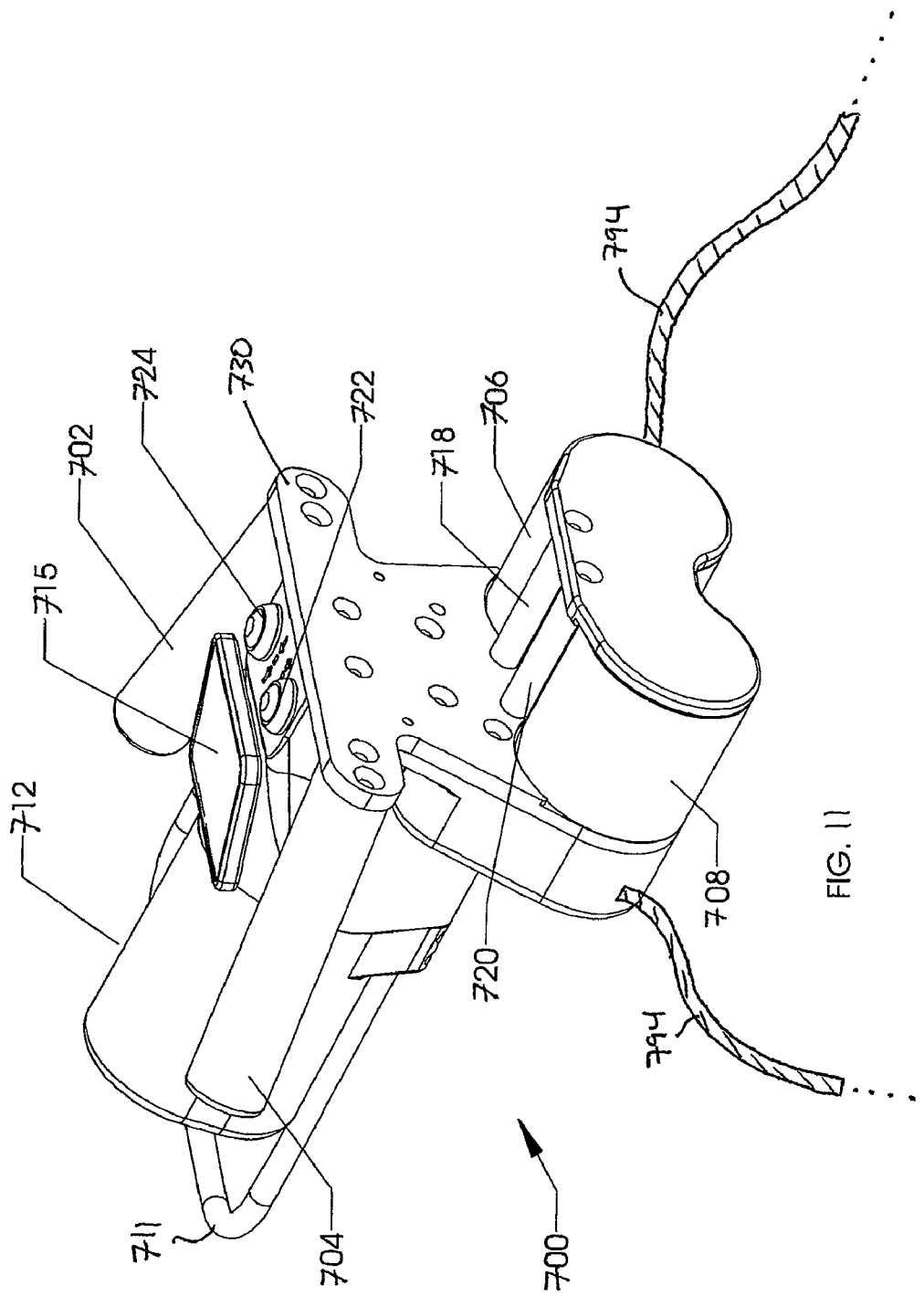
FIG. 11 is another perspective view of the external adjustment device of FIG. 6. Optional adjustable straps are illustrated.

Still referring to FIG. 6, the two magnets 706, 708 are separated from one another. An alignment window 716 is formed between the left post 718 and the right post 720 which is an opening or aperture to directly view placement of the external adjustment device 700 against the patient 100. During use, the operator can actually "see through" this window to better align the external adjustment device 700 with the patient. For example, a lump may be seen on the skin of the patient 100 where the magnetic assembly 210 of the distraction device 200 is implanted. FIG. 7 illustrates a rear view of the external adjustment device 700 while FIG. 8 illustrates a front view of the external adjustment device 700. A bottom view of the external adjustment device 700 is provided in FIG. 9 while FIGS. 10 and 11 illustrate different perspective views of the external adjustment device 700.

Figure 12:
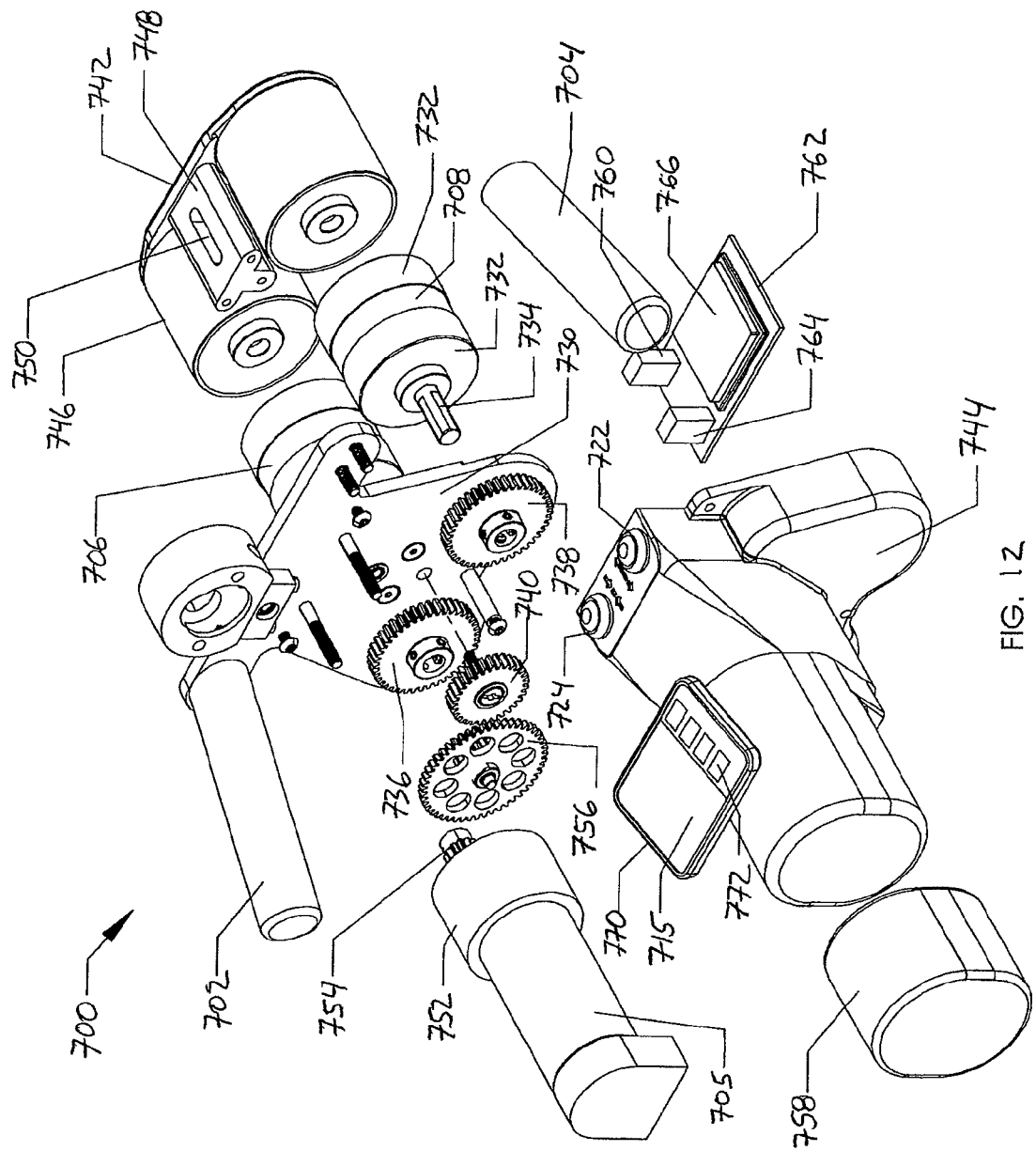
FIG. 12 is an exploded view of another embodiment of an external adjustment device.

The motor 705 of the external adjustment device 700 may turn the cylindrical magnets 706, 708 using the belt/pulley system disclosed in U.S. patent application Ser. Nos. 12/121, 355 and 12/250,442. FIG. 12, however, illustrates an alternative drive system that uses a series of gears 736, 738, 740, 754, 756. As seen in FIG. 12, the external adjustment device 700 contains two magnets 706, 708, which are cylindrical in shape and made from rare earth magnets as described herein. The magnets 706, 708 may be diametrically magnetized. The magnets 706, 708 are bonded or attached by other means within magnetic cups 732. The magnetic cups 732 include respective shafts 734 (only one of which can be seen in FIG. 12) which are attached, respectively, to a first magnet gear 736 and a second magnet gear 738. The orientation of the poles of each the two magnets 706, 708 are maintained in relation to each other by means of the gearing system by use of center gear 740, which meshes with both first magnet gear 736 and second magnet gear 738. For example, it may be desired that the south pole of one of the magnets 706 is facing up whenever the south pole of the other magnet 708 is facing down. This arrangement, for instance, maximizes the torque that can be placed on the magnetic assembly 210 of the particular distraction device 200, 272.

Still referring to FIG. 12, the magnets 706, 708 are held between a support member 730 and a front plate 742. On the backside of the external adjustment device 700, a cover or housing 744 contains the motor 705 and gears 736, 738, 740, 754, 756. The magnets 706, 708 rotate within a static magnet cover 746, so that the external adjustment device 700 may be rested directly on the patient 100, while not imparting any motion to the external surfaces of the patient 100. Prior to distracting the distraction device (e.g., spinal, bone, or other) the operator places the external adjustment device 700 over the patient 100 near the location of the implanted magnetic assembly 210. A magnet standoff 748 contains a viewing window 750, analogous to alignment window 716 of FIG. 6, to aid in the placement. To perform a distraction operation, the operator holds the external adjustment device 700 by its handles 702, 704 and depresses a distract switch 722, causing motor 705 to drive in a first direction. The motor 705 has a gear box 752 which causes the rotational speed of an output gear 754 disposed on a shaft (not shown) to be different from the rotational speed of the motor 705 (for example, a slower speed). The output gear 754 then turns a reduction gear 756 which meshes with center gear 740, causing it to turn at a different rotational speed than the reduction gear 756. The center gear 740 meshes with both the first magnet gear 736 and the second magnet gear 738 turning both at a rate which is identical to each other. Depending on the particular location on the patient 100 where the magnets 706, 708 of the external adjustment device 700 are located, it is desired that this rate be controlled, to minimize the current density though the tissues and fluids of the body.

For example a rotational speed of 35 RPM or less for the magnets 706, 708 is contemplated to keep current densities at a desirable level. At any time, the distraction may be lessened by depressing the retraction button 724. For example, if the patient feels significant pain, or numbness in the area being lengthened, the operator can depress retraction button 724 to reverse the distraction operation. FIG. 12 illustrates a rechargeable battery 758 that may optionally be employed to supply power to the external adjustment device 700. As explained herein, the external adjustment device 700 may be alternatively powered using power cord 711. The rechargeable battery 758 may also be an emergency power source in the event that conventional AC power is unavailable.

Still referring to FIG. 12, the on and off commands to the motor 705 are achieved by a first micro-relay 760 located on a circuit board 762. The directional (clockwise/counterclockwise) commands to the motor are achieved by a second micro-relay 764, also located on the circuit board 762. A microcontroller 766 allows the mechanical inputs to the distraction button 722 and retraction button 724 to operate the rotation of the magnets 706, 708 by means of the micro-relays 760 and 764. A control panel 770 having the display 715 and input buttons 772 is shown on top of the external adjustment device 700. Inputs to the external adjustment device 700 may be achieved by using the input buttons 772, or by using a GUI (graphical user interface) which is a feature of the display 715. The microcontroller 766 may loaded with software that locks-out or prevents over distraction of the device 200, 272. The microcontroller may also receive inputs to the external adjustment device 700 via the input buttons 772 or GUI on the display 715 (e.g., through touch-screen, mouse-like device, buttons, etc.). The board 762, microcontroller 766 and micro-relays 760, 764 can all be contained within the housing 744, or even as a part of the control panel 770.

Figure 13:
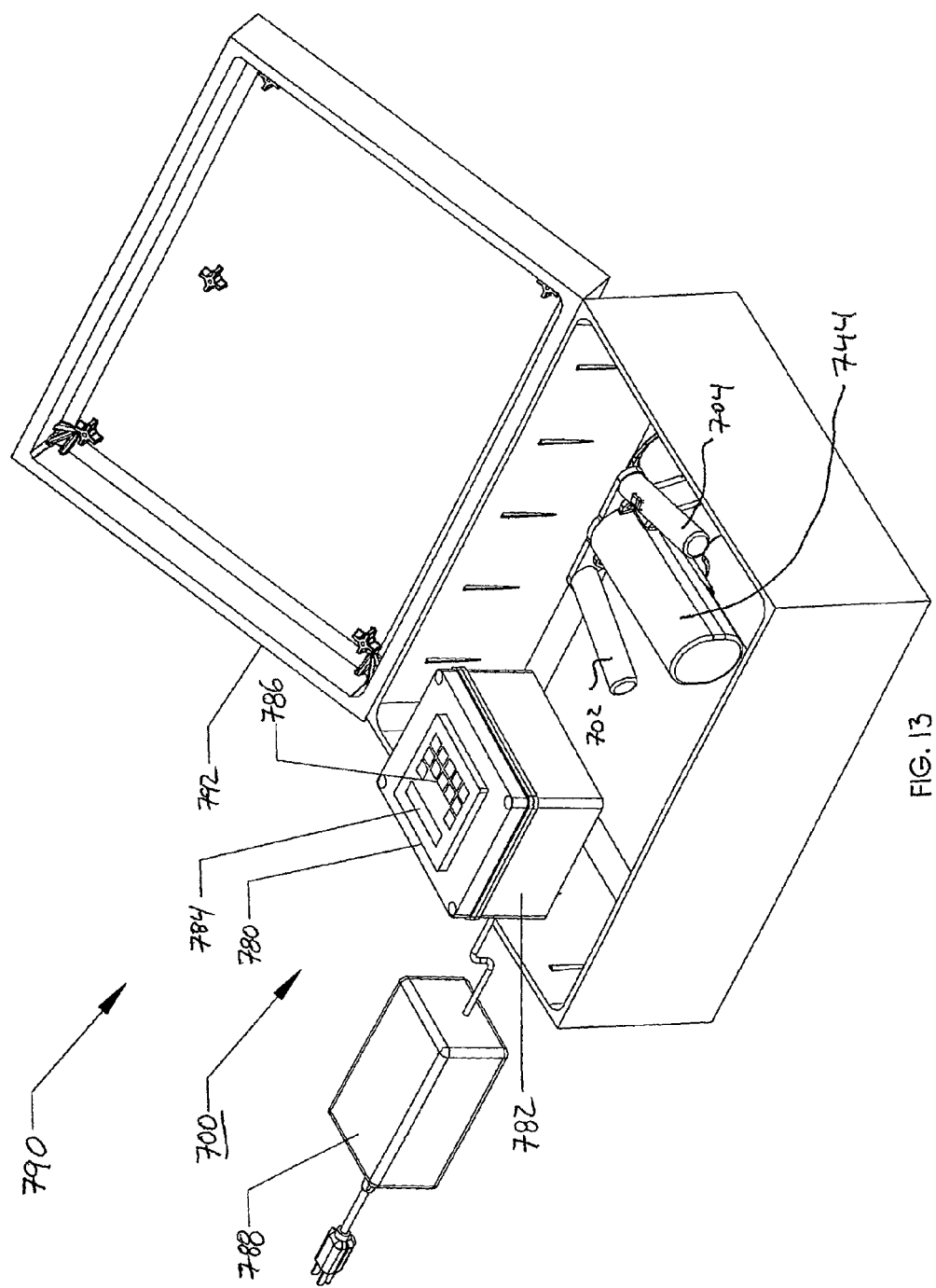
FIG. 13 is a perspective view of a protective case of an external adjustment device.

Alternatively, as illustrated in FIG. 13, a separate programmable logic controller (PLC) 780 can be used, and may be located in a different enclosure 782 which contains a display 784 and input buttons 786. Still referring to FIG. 13, the external adjustment device 700 in this embodiment includes a power supply 788 stored and protected inside a storage case 790 having a closable lid 792. There is enough padding at the bottom, sides and top of the storage case 790 so that the powerful cylindrical magnets 706, 708 are sufficiently spaced apart from the external walls of the storage case 790, so that when the storage case 790 has its lid 792 closed, the magnetic field at the external walls of the storage case 790 are small enough so that they will not cause damage to electrical equipment or significantly attract metal objects. This way, magnet safety can be easily practiced. Preferably, the distance is controlled so that the magnetic field strength is less than 0.002 Gauss at a distance of 2.1 meters from any point on the external surface of the storage case 790 in order to not be considered "Magnetic Material" by International Air Transport Association (IATA) regulations. Alternatively, shielding material, such as mu-metal (a nickel-iron alloy of about 75% nickel, 15% iron, plus copper and molybdenum) may be used in the wall of the storage case 790. In this embodiment, the cylindrical magnets 706, 708 may be mechanically uncoupled from the strong attraction shielding material using a clip(s), un-fastener(s), release(s), prying wedge(s), or the like.

The external adjustment device 700 may be used by healthcare personnel at an outpatient facility, physician's office or the like. Alternatively, the external adjustment device 700 may be used by family members within the home of the patient 100. The microcontroller 766 or PLC 780 have the capability of allowing the physician to program in limits so that the patient cannot be, for example, over-distracted by operator error, mistake, or misuse. The physician may also create commands that are read on the display by the family members. For example, "distract 1 mm today" may be visible to the operator via the display 715. The ability to program in limits of this sort, or other commands is password protected, so that it cannot be changed by unauthorized persons. For example, while the external adjustment device 700 may be capable of performing any number of operations (e.g., unlimited distraction or multiple distractions over a small period of time), the microcontroller 766 or PLC 780 may be set by the physician to allow only certain commands when the external adjustment device 700 is used in a home setting. For example, the total distraction length in any particular use may be limited. This pre-set distance may be stored in the microcontroller 766 or PLC 780. As still another example, distraction intervals may be set in the external adjustment device 700 (e.g., adjustment permitted only after a few weeks have passed since last distraction) to ensure patient safety during home use. This pre-set time may be stored in the microcontroller 766 or PLC 780. In this regard, the microcontroller 766 or PLC 780 may have an internal clock that can be used to determine the elapsed time between distraction events. The microcontroller 766 or PLC 780 may also be programmed to completely lockout users if improper use is detected. For example, excessive use of the retraction button 724 may cause the microcontroller 766 or PLC 780 to lock-out the at home user until the external adjustment device 700 is returned to the physician's office.

Additionally, the external adjustment device 700 may be connected either through a wired (e.g., USB or other network cable) or wireless connection to a remote office network, for example, allowing the physician to reprogram the device without the patient 100 having to bring the external adjustment device 700 into the office. For example, the external adjustment device 700 could use the modem of a separate personal computer to transmit and receive data between the device 700 and a remote network location. In this regard, the physician is also able to download data from the device 700. Certain features of the external adjustment device 700 may be turned on or off remotely using such a connection. The patient 100 may also have an implanted RFID (Radio Frequency Identification) chip that allows in the information to be read and written directly to the RFID chip. For example, patient demographics, implant length, distraction amount, distraction force, time, date, and the like may be stored on the RFID chip.

When the patient 100 is having his or her spine distraction performed, they may lie prone, and may even have a pillow, pad, roll or shaped convex v-block below their torso, in order to further aid in the distraction of the spine, or lower the requirement of the distraction force (or magnet torque) that needs to be achieved. Though it has been described that lengthening procedures for the spine occur when the patient is lying prone, the patient may also be in a standing position or hanging, for example by the shoulders. This latter arrangement adds some traction to the spine, thus aiding the distraction. Full traction may even be employed. Alternatively, the patient 100 may be sitting while the adjustment is done, and the external adjustment device 700 may also be built into a chair or seat or configured to be removably secured to a chair or seat. For example the magnets 706, 708 may protrude from the backrest, with their axes aligned vertically. The patient simply sits down and leans back against the magnet cover 746.

When used in conjunction with a limb lengthening device 272 such as that illustrated in FIG. 5, the external adjustment device 700 may have one or more adjustable straps 794 as illustrated in FIG. 11 that hold the external adjustment device 700 it to the limb. The straps 794 could include a material such as VELCRO or the like to permit easy adjustment. Alternatively, a conventional type buckle may be used to secure the straps 794 around the particular limb of the patient 100.

Figure 14:
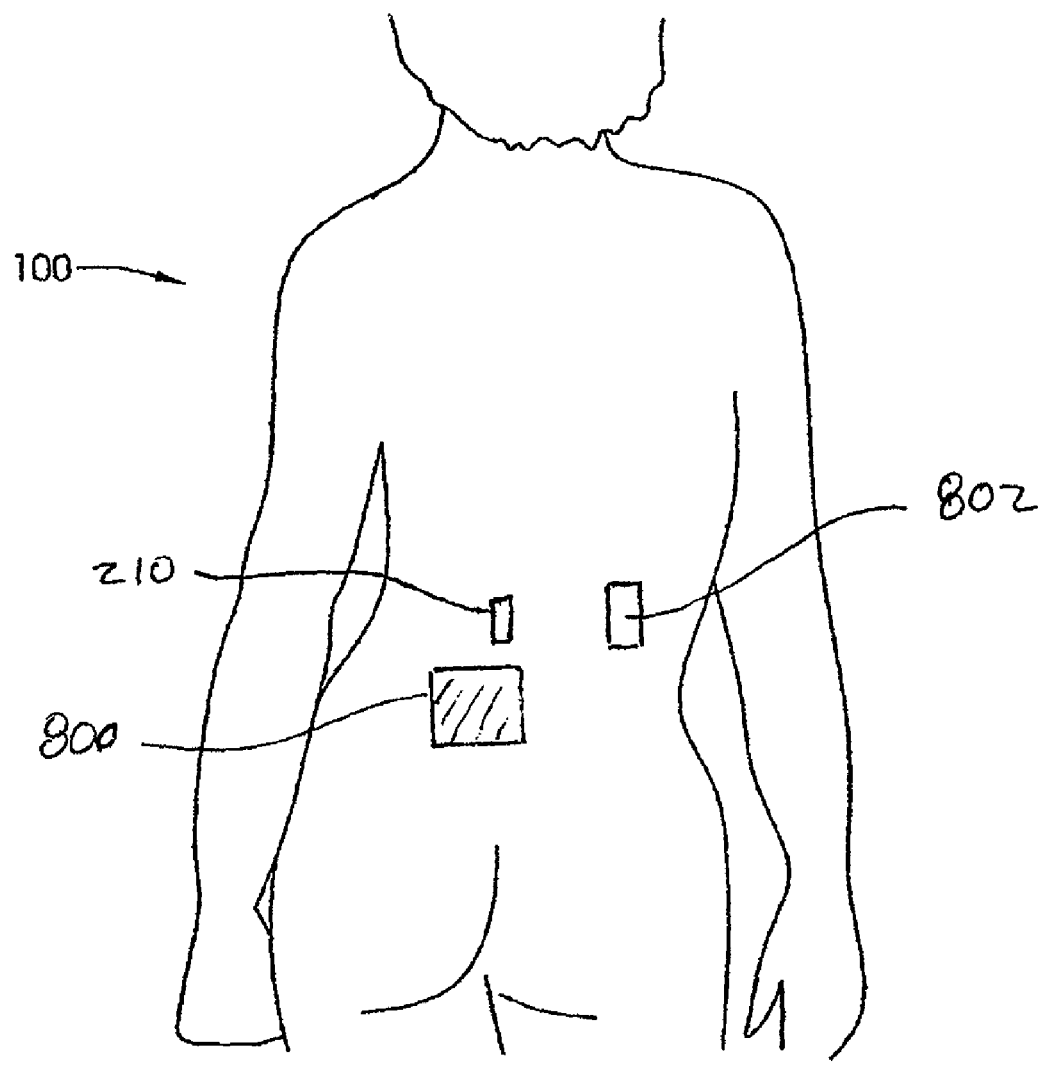
FIG. 14 illustrates a view of a patient in position for an adjustment procedure.

Referring to FIG. 14, an exemplary method and apparatus for determining the location of an implanted magnet in a patient 100 is described. As seen in FIG. 14, a piece of magnetic viewing sheet 800 is used to view the orientation of the magnetic fields. The areas of high magnetic intensity appear dark, while the transition zones (areas where the poles are changing, also known as the neutral zone) appear light. In other words, the magnetic viewing sheet 800 turns dark when the field lines are perpendicular to the surface, and it turns light when the field lines are horizontal, i.e., across the surface. If a magnet is placed under it, as would the case be when the sheet 800 is placed over the patient 100 having an implanted distraction device with a magnetic assembly 210, with one of the poles facing the film, it will show the magnet as dark with a light outline. The magnetic viewing sheet 800 is a translucent sheet that has small particles of a ferromagnetic material suspended in the cells of the sheet. The magnetic viewing sheet 800 may be made of a polymer material or even paper products (e.g., wood-based materials) with ferromagnetic material embedded therein.

In FIG. 14, a patient 100 lies, for example in a prone position and the medical personnel (or family member) who will perform the adjustment places the magnetic viewing sheet 800 on the surface of the patient's skin or clothes and moves the sheet 800 until the magnetic field from the magnetic assembly 210 of the distraction device is identified. The skin or clothes may be marked, or the magnetic viewing sheet 800 may simply be left in place as a visual indicator. Turning to FIG. 6, the alignment window 716 located between left post 718 and right post 720 of the external adjustment device 700 is centered over the indicated location of the magnetic assembly 210 and the external adjustment device 700 is held by grasping the left handle 702 with the left hand and the right handle 704 with the right hand. Because the axial center of mass 714 of the external adjustment device 700 is located substantially at the base of each of the two handles 702, 704, in most non-obese patients, the attraction between the left and right cylindrical magnets 706, 708 and the magnetic assembly 210 can be sensed by the hands. In particular, the hands can sense the magnetic pull or attractive force between the magnetic assembly 210 and the cylindrical magnets 706, 708. Therefore, the magnetic assembly 210 can also be located without the use of magnetic viewing sheet 800. In any patient 100, but especially in obese patients, the external adjustment device 700 can be pressed down with a firm, though not painful, force in order to compress fat and other tissue and thus to decrease the distance between the left and right cylindrical magnets 706, 708 and the magnetic assembly 210. This will increase the maximum torque that can be delivered to the magnetic assembly 210, and thus the distraction force that can be applied.

As an alternative to placing the magnetic viewing sheet 800 or using the balance feature of the external adjustment device 700, a locating magnet 802 may be placed against the skin or clothing of the patient 100. The locating magnet 802 will be most attracted or, alternatively, repulsed to the area near the magnetic assembly 210, and thus give an indication of its location and orientation.

While embodiments have been shown and described, various modifications may be made without departing from the scope of the inventive concepts disclosed herein. The invention(s), therefore, should not be limited, except to the following claims, and their equivalents.

What is claimed is:

1. A method of confirming the location of an implanted magnetic assembly comprising:
   identifying the general region of the patient where the implanted magnetic assembly is believed to be located;
   moving an external adjustment device adjacent to the patient in the general region, the external adjustment device comprising a support member having first and second cylindrical magnets disposed on one side thereof and a pair of handles disposed on an opposing side thereof along with a motor configured to rotate the first and second cylindrical magnets, wherein a center of mass of the external adjustment device is located substantially at a base of the pair of handles adjacent to the support member; and
   sensing the location of the implanted magnetic assembly by detecting magnetic attraction of the external adjustment device toward the patient.

2. The method of claim 1, further comprising visually confirming the location by locating a lump in the skin of the patient.

3. A method of confirming the location of an implanted magnetic assembly comprising:
   identifying the general region of the patient where the implanted magnetic assembly is believed to be located;
   moving an external adjustment device adjacent to the patient in the general region, the external adjustment device comprising a support member having first and second cylindrical magnets disposed on one side thereof and separated by a viewing aperture interposed there between, the external adjustment device further comprising a pair of handles disposed on an opposing side thereof along with a motor configured to rotate the first and second cylindrical magnets; and
   identifying the location of the implanted magnetic assembly by moving the external adjustment device in the general region and at least partially viewing the general region through the viewing aperture to identify a lump.

4. A method of confirming the location of an implanted magnetic assembly comprising:
   identifying the general region of the patient where the implanted magnetic assembly is believed to be located;
   moving an external adjustment device adjacent to the patient in the general region, the external adjustment device comprising first and second handle portions and first and second cylindrical magnets disposed between the first and second handle portions; and
   sensing the location of the implanted magnetic assembly by detecting magnetic attraction of the external adjustment device toward the patient.

5. The method of claim 4, further comprising viewing the location of the implanted magnetic assembly by moving the external adjustment device in the general region and at least partially viewing the general region through a viewing aperture interposed between the first and second cylindrical magnets to identify a lump.

* * * * *